US007105719B1

(12) United States Patent
Ashikari et al.

(10) Patent No.: US 7,105,719 B1
(45) Date of Patent: *Sep. 12, 2006

(54) GENE ENCODING A PROTEIN HAVING ACYL GROUP TRANSFER ACTIVITY

(75) Inventors: Toshihiko Ashikari, Takatsuki (JP);
Yoshikazu Tanaka, Otsu (JP);
Hiroyuki Fujiwara, Neyagawa (JP);
Masahiro Nakao, Nagaokakyo (JP);
Yuko Fukui, Osaka (JP); Keiko Sakakibara, Takatsuki (JP); Masako Mizutani, Kyoto (JP); Takaaki Kusumi, Suita (JP)

(73) Assignee: Suntory Limited, Osaka (JP)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 08/894,356

(22) PCT Filed: Feb. 16, 1996

(86) PCT No.: PCT/JP96/00348

§ 371 (c)(1),
(2), (4) Date: Aug. 18, 1997

(87) PCT Pub. No.: WO96/25500

PCT Pub. Date: Aug. 22, 1996

(30) Foreign Application Priority Data

Feb. 17, 1995 (JP) .................................. 7-067159
Jun. 29, 1995 (JP) .................................. 7-196915
Jan. 30, 1996 (JP) .................................. 8-046534

(51) Int. Cl.
*C12N 15/09* (2006.01)
*C12N 15/29* (2006.01)
*C12N 15/82* (2006.01)
*A01H 5/00* (2006.01)

(52) U.S. Cl. ...................... 800/278; 800/298; 800/295; 435/320.1; 435/468; 435/69.1

(58) Field of Classification Search ............... 536/23.6, 536/23.2; 435/69.1, 172.2, 352.1, 410, 320.1, 435/468; 800/278, 282, 295, 298
See application file for complete search history.

(56) References Cited

U.S. PATENT DOCUMENTS 5,349,125 A  9/1994 Holton et al.

FOREIGN PATENT DOCUMENTS

EP         522 880      1/1994
WO         WO93/14211   7/1993
WO         WO93/20206   10/1993
WO         WO94/03591 * 2/1994

OTHER PUBLICATIONS

Ishizaki et al. FEBS Letter. 1988. vol. 10:424-430.*
Matern et al. Arch. Bioch. Biophys. 1981. vol. 208:233.*
Kamsteeg et al. Bioch. Physiol. Pflanzen. 1980. vol. 175:403.*
Heidmann et al. Nature. 1987. vol. 330:677-678.*
Napoli et al. 1989. vol. 2:278-289.*
Boase et al. In vitro Cell. Deve. Bio. 1998. vol. 34: 46-51.*
Carvalho et al. The EMBO J. 1992. vol. 11:2595-2602.*
Lopez-Serrano et al. Journal of Agriculture Food Chemistry. 1999. Mar. 47:3 824-827.*
Lazar et al. Mol. Cell. Biol., vol. 8, pp. 1247-1252, 1988.*
Kazuki Saito et al., "Acyltransferases for Lupin Alkaloids in Lupinus Hirsutus", *Phytochemistry*, vol. 32, No. 1, pp. 87-91 (1993).
Jonathan Negrel et al., "Purification and Properties of Putrescine Hydroxycinnamoyl Transferase from Tobacco (*Nicotiana tabacum*) Cell Suspensions", *Plant. Physiol.* vol. 98, pp. 1264-1269 (1992).
Sanua Lotfy et al., "Formation of w-Feruloyloxypalmitic Acid by an Enzyme from Wound-healing Potato Tuber Discs", *Phytochemistry*, vol. 35, No. 6, pp. 1419-1424 (1994).
Samia Lotfy et al., "Partial Purification and Characterization of Hydroxycinnamoyl CoA: Transferases from Apple and Date Fruits", *Phytochemistry*, vol. 31, No. 3, pp. 767-772 (1992).
Veronique Louis et al., "Tyramine Hydroxycinnamoyl Transferase in the Roots of Wheat and Barley Seedlings", *Phytochemistry*, vol. 30, No. 8, pp. 2519-2522 (1991).
Dieter Strack et al., "Quinolizidine Alkaloids and the Enzymatic Synthesis of Their Cinnamic and Hydroxycinnamic Acid Esters in *Lupinus angustifolius* and *L. leteus*", *Phytochemistry*, vol. 30, No. 5, pp. 1493-1498 (1991).
Colin R. Bird et al, "Agmatine Coumaroyltransferase from Barley Seedlings", *Phytochemistry*, vol. 22, No. 11, pp. 2401-2403 (1983).
Bernard Ulbrich et al., "Partial Purification and Properties of p-Hydroxycinnamoyl-CoA: Shikimate-p-Hydroxy Cinnamoyl Transferase from Higher Plants", *Phytochemistry*, vol. 19, pp. 1625-1629, (1980).
Timothy A. Holton, "Cloning and Expression of Cytochrome P450 genes controlling flower colour", *Nature*, vol. 366, pp. 276-279, Nov. 18, 1993.

(Continued)

*Primary Examiner*—Medina A. Ibrahim
(74) *Attorney, Agent, or Firm*—Drinker Biddle & Reath LLP

(57) ABSTRACT

The invention relates to isolated polynucleotides encoding a protein having aromatic acyltransferase activity, vectors comprising aromatic acyltransferase polynucleotides, and methods of transforming plants with anthocyanin acyltransferase polynucleotides to alter flower colors. The invention also relates to transformed host cells, plants, and flower cuts expressing proteins having anthocyanin acyltransferase activity.

12 Claims, No Drawings

OTHER PUBLICATIONS

Oliver Dangles et al., "Anthocyanin Intramolecular Copigment Effect," *Phytochemistry*, vol. 34, pp. 119-124 (1993).

Werner E. Glabgen et al. "Acylation of Anthocyanins With Hydroxycinnamic Acids via 1-0-Acylglucosides By Protein Preparations From Cell Cultures of *Daucus Carota L,*" *Planta*, vol. 186, pp. 582-585 (1992).

Toshio Goto et al., "Structures and Molecular Stacking of Anthocyanins-Flower Color Variation," *Angew Chem. Int. Ed. Engl.* vol. 30, pp. 17-33 (1991).

John Kamsteeg et al., "Identification, Properties and Genetic Control of Hydroxycinnamoyl-coenzyme A: Anthocyanidin 3-rhamnosy(1-6) Glucoside, 4'''-hydroxycinnamoyl Transferase Isolated from Petals of *Silene dioica,*" *Biochem. Physiol. Pflanzen* vol. 175, pp. 403-411 (1980).

Marie H. Saylor et al, "Hydroxycinnamoyl: Coenzyme A Transferase Involved in the Biosynthesis of Kaempferol-3-(p-coumaroyl Triglucoside) in *Pisum sativum,*" *Z. Naturforsch*, vol. 32c pp. 765-768, (1977).

Monika Teusch et al., "Genetic Control of Hydroxycinnamoyl-Cenzyme A: Anthocyanidin 3-Glycoside-Hydroxycinnamollytranse From Petals of *Matthiola Incana,*" *Phytochemistry*, vol. 26, No. 4, pp. 991-994 (1987).

Kumi Yoshida, "Intramolecular Stacking Confromation of Gentiodelphin, a Diacylated Anthocyanin from *Gentiana Makinoi,*" *Tetrahedron*, vol. 48, No. 21, pp. 4313-4326, (1992).

Kobayashi et al., "Amidase coupled with low-molecular-mass nitrile hydratase from *Rhodococcus rhodochrous* J1 Sequencing and expression of the gene and purification and characterization of the gene product", Eur. J. Biochem., vol. 217, 1993, pp. 327-336.

* cited by examiner

SEQUENCE LISTING

<160> NUMBER OF SEQ ID NOS: 40

<210> SEQ ID NO 1
<211> LENGTH: 1703
<212> TYPE: DNA
<213> ORGANISM: Gentiana triflora
<220> FEATURE:
<221> NAME/KEY: CDS
<222> LOCATION: (6)..(1412)

<400> SEQUENCE: 1

```
tcatt atg gag caa atc caa atg gtg aag gtt ctt gaa aaa tgc caa gtt      50
      Met Glu Gln Ile Gln Met Val Lys Val Leu Glu Lys Cys Gln Val
       1               5                   10                  15 aca cca cca tct gac aca aca gat gtc gag tta tcg cta ccg gta aca      98
Thr Pro Pro Ser Asp Thr Thr Asp Val Glu Leu Ser Leu Pro Val Thr
                 20                  25                  30 ttc ttc gat atc ccc tgg ttg cac ttg aat aag atg cag tcc ctt ctg     146
Phe Phe Asp Ile Pro Trp Leu His Leu Asn Lys Met Gln Ser Leu Leu
             35                  40                  45 ttt tac gac ttt ccg tac cca aga aca cat ttc ttg gac act gtt atc     194
Phe Tyr Asp Phe Pro Tyr Pro Arg Thr His Phe Leu Asp Thr Val Ile
         50                  55                  60 cct aat ctt aag gcc tct ttg tct ctc act cta aaa cac tac gtt ccg     242
Pro Asn Leu Lys Ala Ser Leu Ser Leu Thr Leu Lys His Tyr Val Pro
     65                  70                  75 ctt agc gga aat ttg ttg atg ccg atc aaa tcg ggc gaa atg ccg aag     290
Leu Ser Gly Asn Leu Leu Met Pro Ile Lys Ser Gly Glu Met Pro Lys
 80                  85                  90                  95 ttt cag tac tcc cgt gat gag ggc gac tcg ata act ttg atc gtt gcg     338
Phe Gln Tyr Ser Arg Asp Glu Gly Asp Ser Ile Thr Leu Ile Val Ala
                100                 105                 110 gag tct gac cag gat ttt gac tac ctt aaa ggt cat caa ctg gta gat     386
Glu Ser Asp Gln Asp Phe Asp Tyr Leu Lys Gly His Gln Leu Val Asp
            115                 120                 125 tcc aat gat ttg cat ggc ctt ttt tat gtt atg cca cgg gtt ata agg     434
Ser Asn Asp Leu His Gly Leu Phe Tyr Val Met Pro Arg Val Ile Arg
        130                 135                 140 acc atg caa gac tat aaa gtg atc ccg ctc gta gcc gtg caa gta acc     482
Thr Met Gln Asp Tyr Lys Val Ile Pro Leu Val Ala Val Gln Val Thr
    145                 150                 155 gtt ttt cct aac cgt ggc ata gcc gtg gct ctg acg gca cat cat tca     530
Val Phe Pro Asn Arg Gly Ile Ala Val Ala Leu Thr Ala His His Ser
160                 165                 170                 175 att gca gat gct aaa agt ttt gta atg ttc atc aat gct tgg gcc tat     578
Ile Ala Asp Ala Lys Ser Phe Val Met Phe Ile Asn Ala Trp Ala Tyr
                180                 185                 190 att aac aaa ttt ggg aaa gac gcg gac ttg ttg tcc gcg aat ctt ctt     626
Ile Asn Lys Phe Gly Lys Asp Ala Asp Leu Leu Ser Ala Asn Leu Leu
            195                 200                 205 cca tct ttc gat aga tcg ata atc aaa gat ctg tat ggc cta gag gaa     674
Pro Ser Phe Asp Arg Ser Ile Ile Lys Asp Leu Tyr Gly Leu Glu Glu
        210                 215                 220
```

| | | | | | | | | | | | | | | | | |
|---|---|---|---|---|---|---|---|---|---|---|---|---|---|---|---|---|
| aca | ttt | tgg | aac | gaa | atg | caa | gat | gtt | ctt | gaa | atg | ttc | tct | aga | ttt | 722 |
| Thr | Phe | Trp | Asn | Glu | Met | Gln | Asp | Val | Leu | Glu | Met | Phe | Ser | Arg | Phe | |
| | | 225 | | | | 230 | | | | | 235 | | | | | |
| gga | agc | aaa | ccc | cct | cga | ttc | aac | aag | gta | cga | gct | aca | tat | gtc | ctc | 770 |
| Gly | Ser | Lys | Pro | Pro | Arg | Phe | Asn | Lys | Val | Arg | Ala | Thr | Tyr | Val | Leu | |
| 240 | | | | | 245 | | | | | 250 | | | | | 255 | |
| tcc | ctt | gct | gaa | atc | cag | aag | cta | aag | aac | aaa | gta | ctg | aat | ctc | aga | 818 |
| Ser | Leu | Ala | Glu | Ile | Gln | Lys | Leu | Lys | Asn | Lys | Val | Leu | Asn | Leu | Arg | |
| | | | | 260 | | | | | 265 | | | | | 270 | | |
| gga | tcc | gaa | ccg | aca | ata | cgt | gta | acg | acg | ttc | aca | atg | acg | tgt | gga | 866 |
| Gly | Ser | Glu | Pro | Thr | Ile | Arg | Val | Thr | Thr | Phe | Thr | Met | Thr | Cys | Gly | |
| | | 275 | | | | 280 | | | | | 285 | | | | | |
| tac | gta | tgg | aca | tgc | atg | gtc | aaa | tca | aaa | gat | gac | gtc | gta | tca | gag | 914 |
| Tyr | Val | Trp | Thr | Cys | Met | Val | Lys | Ser | Lys | Asp | Asp | Val | Val | Ser | Glu | |
| | | 290 | | | | 295 | | | | | 300 | | | | | |
| gaa | tca | tcg | aac | gac | gaa | aat | gag | ctc | gag | tac | ttc | agt | ttt | aca | gcg | 962 |
| Glu | Ser | Ser | Asn | Asp | Glu | Asn | Glu | Leu | Glu | Tyr | Phe | Ser | Phe | Thr | Ala | |
| | 305 | | | | | 310 | | | | | 315 | | | | | |
| gat | tgc | cga | gga | ctt | ctg | acg | ccc | cgt | ccg | cct | aac | tac | ttt | ggc | | 1010 |
| Asp | Cys | Arg | Gly | Leu | Leu | Thr | Pro | Pro | Cys | Pro | Pro | Asn | Tyr | Phe | Gly | |
| 320 | | | | | 325 | | | | | 330 | | | | | 335 | |
| aac | tgt | ctt | gcg | tca | tgc | gtt | gca | aaa | gca | aca | cat | aaa | gag | tta | gtt | 1058 |
| Asn | Cys | Leu | Ala | Ser | Cys | Val | Ala | Lys | Ala | Thr | His | Lys | Glu | Leu | Val | |
| | | | | 340 | | | | | 345 | | | | | 350 | | |
| ggg | gat | aaa | ggg | ctt | ctt | gtt | gca | gtt | gca | gct | att | gga | gaa | gcc | att | 1106 |
| Gly | Asp | Lys | Gly | Leu | Leu | Val | Ala | Val | Ala | Ala | Ile | Gly | Glu | Ala | Ile | |
| | | | 355 | | | | | 360 | | | | | 365 | | | |
| gaa | aag | agg | ttg | cac | aac | gaa | aaa | ggc | gtt | ctt | gca | gat | gca | aaa | act | 1154 |
| Glu | Lys | Arg | Leu | His | Asn | Glu | Lys | Gly | Val | Leu | Ala | Asp | Ala | Lys | Thr | |
| | | 370 | | | | | 375 | | | | | 380 | | | | |
| tgg | tta | tcg | gaa | tct | aat | gga | atc | cct | tca | aaa | aga | ttt | ctc | ggg | att | 1202 |
| Trp | Leu | Ser | Glu | Ser | Asn | Gly | Ile | Pro | Ser | Lys | Arg | Phe | Leu | Gly | Ile | |
| 385 | | | | | 390 | | | | | 395 | | | | | | |
| acc | gga | tcg | cct | aag | ttc | gat | tcg | tat | ggt | gta | gat | ttt | gga | tgg | gga | 1250 |
| Thr | Gly | Ser | Pro | Lys | Phe | Asp | Ser | Tyr | Gly | Val | Asp | Phe | Gly | Trp | Gly | |
| 400 | | | | | 405 | | | | | 410 | | | | | 415 | |
| aag | cct | gca | aaa | ttt | gac | att | acc | tct | gtt | gat | tat | gca | gaa | ttg | att | 1298 |
| Lys | Pro | Ala | Lys | Phe | Asp | Ile | Thr | Ser | Val | Asp | Tyr | Ala | Glu | Leu | Ile | |
| | | | | 420 | | | | | 425 | | | | | 430 | | |
| tat | gtg | att | cag | tcc | agg | gat | ttt | gaa | aaa | ggt | gtg | gag | att | gga | gta | 1346 |
| Tyr | Val | Ile | Gln | Ser | Arg | Asp | Phe | Glu | Lys | Gly | Val | Glu | Ile | Gly | Val | |
| | | | 435 | | | | | 440 | | | | | 445 | | | |
| tca | ttg | cct | aag | att | cat | atg | gat | gca | ttt | gca | aaa | atc | ttt | gaa | gaa | 1394 |
| Ser | Leu | Pro | Lys | Ile | His | Met | Asp | Ala | Phe | Ala | Lys | Ile | Phe | Glu | Glu | |
| | | 450 | | | | | 455 | | | | | 460 | | | | |
| ggc | ttt | tgc | tct | ttg | tca | tagtctcttt | aatagaacca | tatttgctgc | | | | | | | | 1442 |
| Gly | Phe | Cys | Ser | Leu | Ser | | | | | | | | | | | |
| | 465 | | | | | | | | | | | | | | | | aataaagtac caagtccttt agtaacacta caccaaaccc tactttcgag gcgggaacac  1502 cacaacgagg ttcaatcact agaaggttgt acttcataaa ttccagaggt cgaatataca  1562 ccgttgtcct ctgaaaagtt gaacctcaca cctgacatgg tgttacgata ggtattgtat  1622 aatgccatta tatacttcca taaagtatcc tatgcaatag agaacatgtt atgtgttaaa  1682 aaaaaaaaaa aaaaaaaaa a  1703

<210> SEQ ID NO 2
<211> LENGTH: 1622
<212> TYPE: DNA

-continued

```
<213> ORGANISM: Gentiana triflora
<220> FEATURE:
<221> NAME/KEY: CDS
<222> LOCATION: (35)..(1471)

<400> SEQUENCE: 2
gaaccattga atccaattaa tctgatttat taag atg gca gga aat tcc gag gat      55
                                     Met Ala Gly Asn Ser Glu Asp
                                      1               5 atc aaa gtt ctt gag aaa tgc cgt gtt gcg cca cca ccg gac gcc gtc      103
Ile Lys Val Leu Glu Lys Cys Arg Val Ala Pro Pro Pro Asp Ala Val
         10                  15                  20 gcc gag ttt aca gtc cca ctg tcg ttt ttc gac atg cga tgg ttg atc      151
Ala Glu Phe Thr Val Pro Leu Ser Phe Phe Asp Met Arg Trp Leu Ile
     25                  30                  35 tct gat gca gaa cac cat ctg cat ttc tac aga ttc cgc cat cct tgt      199
Ser Asp Ala Glu His His Leu His Phe Tyr Arg Phe Arg His Pro Cys
 40                  45                  50                  55 ccc aac tct aaa ttt atc att tca tcc att aaa tcg tcc ctt tcc ctt      247
Pro Asn Ser Lys Phe Ile Ile Ser Ser Ile Lys Ser Ser Leu Ser Leu
                 60                  65                  70 gtt ctc aaa cac ttt ctt ccg tta gcc ggg aat ttg att tgg ccg gta      295
Val Leu Lys His Phe Leu Pro Leu Ala Gly Asn Leu Ile Trp Pro Val
             75                  80                  85 gat tcc tcc gat aga atg ccg gag ttg cgt tac aag aaa ggg gac tcc      343
Asp Ser Ser Asp Arg Met Pro Glu Leu Arg Tyr Lys Lys Gly Asp Ser
         90                  95                 100 gtt tct tta aca att gca gaa tcg agc atg gat ttt gat tat ctc gcc      391
Val Ser Leu Thr Ile Ala Glu Ser Ser Met Asp Phe Asp Tyr Leu Ala
    105                 110                 115 gga gat cat cag agg gat tct tat aaa ttc aac gat ttg att ccg cag      439
Gly Asp His Gln Arg Asp Ser Tyr Lys Phe Asn Asp Leu Ile Pro Gln
120                 125                 130                 135 ctg cca gaa ccg att gta acc tcc ggc gac gaa gta tta cca ctt ttt      487
Leu Pro Glu Pro Ile Val Thr Ser Gly Asp Glu Val Leu Pro Leu Phe
                140                 145                 150 gct tta cag gtg acg gtg ttc tcc aac acc ggt ata tgc att gga cgc      535
Ala Leu Gln Val Thr Val Phe Ser Asn Thr Gly Ile Cys Ile Gly Arg
            155                 160                 165 aat ctt cat caa gtt ctt ggt gat gcc agt tct ttt ctg cat ttt aat      583
Asn Leu His Gln Val Leu Gly Asp Ala Ser Ser Phe Leu His Phe Asn
        170                 175                 180 aaa tta tgg gtt ttg gtt gac aaa tcc aat gga gat tca tta aag ttc      631
Lys Leu Trp Val Leu Val Asp Lys Ser Asn Gly Asp Ser Leu Lys Phe
    185                 190                 195 ctt cca ctt tct tct cta cct atg tac gac aga tct gtg gtg caa gat      679
Leu Pro Leu Ser Ser Leu Pro Met Tyr Asp Arg Ser Val Val Gln Asp
200                 205                 210                 215 cca ttt cat att cgt cga aaa atc tac aat gaa aga aaa ctg ctc aaa      727
Pro Phe His Ile Arg Arg Lys Ile Tyr Asn Glu Arg Lys Leu Leu Lys
                220                 225                 230 tct cag ggc aca cct act gtt cta aat cca gca att tct aaa gat gaa      775
Ser Gln Gly Thr Pro Thr Val Leu Asn Pro Ala Ile Ser Lys Asp Glu
            235                 240                 245 gtt cga gcc acc ttc atc cta cac cct att gat atc atg aag ctc aag      823
Val Arg Ala Thr Phe Ile Leu His Pro Ile Asp Ile Met Lys Leu Lys
        250                 255                 260 aaa ttc att tcg tca aaa aat cgc aac tta acc ggt agt agt aat tat      871
Lys Phe Ile Ser Ser Lys Asn Arg Asn Leu Thr Gly Ser Ser Asn Tyr
    265                 270                 275
```

```
aat ctg tca act ttc acg gtg aca tct gca ctg atc tgg aca tgc ttg      919
Asn Leu Ser Thr Phe Thr Val Thr Ser Ala Leu Ile Trp Thr Cys Leu
280                 285                 290                 295 tcg aaa tca tta gac acc gtc gta aga gag aag gtg gaa gag gat aaa      967
Ser Lys Ser Leu Asp Thr Val Val Arg Glu Lys Val Glu Glu Asp Lys
            300                 305                 310 cat gca gca aac tta tgt gct ttc atc aac tgc cga caa cgt ttt gct     1015
His Ala Ala Asn Leu Cys Ala Phe Ile Asn Cys Arg Gln Arg Phe Ala
        315                 320                 325 ccg ccg ata cct caa aat tac ttt gga aat tgc ata gtg cct tgt atg     1063
Pro Pro Ile Pro Gln Asn Tyr Phe Gly Asn Cys Ile Val Pro Cys Met
    330                 335                 340 gtg gga tcg act cat gag caa ctt gta gga aat gaa ggg ttg tcg gta     1111
Val Gly Ser Thr His Glu Gln Leu Val Gly Asn Glu Gly Leu Ser Val
345                 350                 355 gct gca acc gcc atc gga gat gct atc cat aag agg tta cat gac tac     1159
Ala Ala Thr Ala Ile Gly Asp Ala Ile His Lys Arg Leu His Asp Tyr
360                 365                 370                 375 gaa gga att ctg aga gga gat tgg ata tcg ccg ccc cga tca aca tct     1207
Glu Gly Ile Leu Arg Gly Asp Trp Ile Ser Pro Pro Arg Ser Thr Ser
            380                 385                 390 gcg gca cca agg tcg acg ctc att tat gtc gtt gga tcc gca caa cgc     1255
Ala Ala Pro Arg Ser Thr Leu Ile Tyr Val Val Gly Ser Ala Gln Arg
        395                 400                 405 aat gtg cat gat ttt gat gca gat ttt ggt tgg gga aag ctt gaa aag     1303
Asn Val His Asp Phe Asp Ala Asp Phe Gly Trp Gly Lys Leu Glu Lys
    410                 415                 420 cat gaa tct gtt tca act aat cct tcg gca aca cta att ttg atc tct     1351
His Glu Ser Val Ser Thr Asn Pro Ser Ala Thr Leu Ile Leu Ile Ser
425                 430                 435 cgg tcc aga aga ttt aaa gga gca ctt gag ctt ggc att tct ttg cct     1399
Arg Ser Arg Arg Phe Lys Gly Ala Leu Glu Leu Gly Ile Ser Leu Pro
440                 445                 450                 455 aag aat agg atg gac gca ttt gcc acc att ttt acg aat ttc atc aat     1447
Lys Asn Arg Met Asp Ala Phe Ala Thr Ile Phe Thr Asn Phe Ile Asn
            460                 465                 470 agt ctc cat gtg agg agc cct ttg taagaaaaaa gtggtatcaa tgtataaaaa    1501
Ser Leu His Val Arg Ser Pro Leu
        475 agacagacaa gttatgatgc aacaaatgtt ttaggagatt acaaatccat gggaagatgt   1561 atcaaactca tctctctata tatatatatt caattgtttt aaaaaaaaaa aaaaaaaaa    1621 a                                                                   1622

<210> SEQ ID NO 3
<211> LENGTH: 1605
<212> TYPE: DNA
<213> ORGANISM: Petunia hybrida
<220> FEATURE:
<221> NAME/KEY: CDS
<222> LOCATION: (67)..(1410)

<400> SEQUENCE: 3
tgtcgacgaa atccatttca tttcctcttc tttcttgttt ttctaatttc gtcatcattg     60 ttatcc atg gca ggt gaa gta gca aaa caa gaa gtt aca aaa gtg aaa       108
       Met Ala Gly Glu Val Ala Lys Gln Glu Val Thr Lys Val Lys
       1               5                   10 gtc ctg aaa aaa aca aac gtg aaa cca cat aaa cca cta gga aaa aaa      156
Val Leu Lys Lys Thr Asn Val Lys Pro His Lys Pro Leu Gly Lys Lys
15                  20                  25                  30
```

-continued

| | |
|---|---|
| gag tgt caa ttg gta aca ttt gat ctt cct tac cta gct ttc tat tac<br>Glu Cys Gln Leu Val Thr Phe Asp Leu Pro Tyr Leu Ala Phe Tyr Tyr<br>                    35                            40                        45 | 204 |
| aac caa aaa ttt ctc atc tat aaa ggt gct gaa aac ttt gac gag acg<br>Asn Gln Lys Phe Leu Ile Tyr Lys Gly Ala Glu Asn Phe Asp Glu Thr<br>              50                          55                          60 | 252 |
| gtg gaa aaa att aaa gat gga ctg gcc tta gta ttg gtg gat ttc tat<br>Val Glu Lys Ile Lys Asp Gly Leu Ala Leu Val Leu Val Asp Phe Tyr<br>65                          70                            75 | 300 |
| caa cta gct ggg aaa ctt gga aaa gat gaa gaa ggg gtt ttc agg gtg<br>Gln Leu Ala Gly Lys Leu Gly Lys Asp Glu Glu Gly Val Phe Arg Val<br>        80                        85                          90 | 348 |
| gaa tac gac gat gac atg gat ggt gta gag gtg aca gtg gct gtt gca<br>Glu Tyr Asp Asp Asp Met Asp Gly Val Glu Val Thr Val Ala Val Ala<br>95                        100                        105                  110 | 396 |
| gaa gag ata gaa gtt gca gat ctt act gat gaa gaa ggc acc acc aaa<br>Glu Glu Ile Glu Val Ala Asp Leu Thr Asp Glu Glu Gly Thr Thr Lys<br>                    115                        120                  125 | 444 |
| ttg cag gac ttg att cct tgt aat aaa atc ttg aat ttg gaa ggg ctt<br>Leu Gln Asp Leu Ile Pro Cys Asn Lys Ile Leu Asn Leu Glu Gly Leu<br>            130                        135                        140 | 492 |
| cat cgc cct ctt cta gct gtg cag ctc acc aag ctc aag gac ggg ctc<br>His Arg Pro Leu Leu Ala Val Gln Leu Thr Lys Leu Lys Asp Gly Leu<br>              145                        150                        155 | 540 |
| acc atg gga tta gca ttt aac cat gct gtg ctg gat ggt act tcg acg<br>Thr Met Gly Leu Ala Phe Asn His Ala Val Leu Asp Gly Thr Ser Thr<br>160                        165                        170 | 588 |
| tgg cac ttt atg acc tcg tgg tcc gag ctt tgc tgt ggg tcc acc tca<br>Trp His Phe Met Thr Ser Trp Ser Glu Leu Cys Cys Gly Ser Thr Ser<br>175                        180                        185                  190 | 636 |
| att tct gtc cca cca ttc ctt gaa cga acc aag gct cgt aac act cga<br>Ile Ser Val Pro Pro Phe Leu Glu Arg Thr Lys Ala Arg Asn Thr Arg<br>                  195                        200                        205 | 684 |
| gtc aag ctc aac ctc tct caa cca tca gat gca ccc gaa cat gct aag<br>Val Lys Leu Asn Leu Ser Gln Pro Ser Asp Ala Pro Glu His Ala Lys<br>          210                        215                        220 | 732 |
| tca gca acc aac ggt gat gtc ccg gcc aac gta gac cca cct ctt cgc<br>Ser Ala Thr Asn Gly Asp Val Pro Ala Asn Val Asp Pro Pro Leu Arg<br>            225                        230                        235 | 780 |
| gaa aga gta ttc aag ttc tcc gag tta gca att gac aaa atc aag tca<br>Glu Arg Val Phe Lys Phe Ser Glu Leu Ala Ile Asp Lys Ile Lys Ser<br>240                        245                        250 | 828 |
| aca gtc aat gcc aac tca gga gag acg cca ttc tcc aca ttc caa tca<br>Thr Val Asn Ala Asn Ser Gly Glu Thr Pro Phe Ser Thr Phe Gln Ser<br>255                        260                        265                  270 | 876 |
| ctc tcc gca cac gtg tgg cta gcc gtc aca cgt gcg cgc caa ctc aag<br>Leu Ser Ala His Val Trp Leu Ala Val Thr Arg Ala Arg Gln Leu Lys<br>              275                        280                        285 | 924 |
| ccc gag gac tac act gtg tac act gtg ttt gct gat tgc agg aaa agg<br>Pro Glu Asp Tyr Thr Val Tyr Thr Val Phe Ala Asp Cys Arg Lys Arg<br>                  290                        295                        300 | 972 |
| gtt gat cct cca atg cca gaa agt tac ttc ggc aac cta att cag gca<br>Val Asp Pro Pro Met Pro Glu Ser Tyr Phe Gly Asn Leu Ile Gln Ala<br>          305                        310                        315 | 1020 |
| att ttc aca gtg acc gcg gca ggt ttg tta cta gca agc ccg atc gag<br>Ile Phe Thr Val Thr Ala Ala Gly Leu Leu Leu Ala Ser Pro Ile Glu<br>            320                        325                        330 | 1068 |
| ttc gct ggt ggg atg ata caa caa gcg atc gtg aag cat gac gct aag<br>Phe Ala Gly Gly Met Ile Gln Gln Ala Ile Val Lys His Asp Ala Lys<br>335                        340                        345                  350 | 1116 |

-continued

```
gcc att gat gaa aga aac aag gag tgg gag agc aac ccg aag atc ttt      1164
Ala Ile Asp Glu Arg Asn Lys Glu Trp Glu Ser Asn Pro Lys Ile Phe
            355                 360                 365 cag tac aaa gat gct gga gtg aac tgt gtt gct gtt gga agt tcg cca      1212
Gln Tyr Lys Asp Ala Gly Val Asn Cys Val Ala Val Gly Ser Ser Pro
        370                 375                 380 agg ttc aag gtt tac gac gtg gat ttt gga tgg gga aag cca gag agt      1260
Arg Phe Lys Val Tyr Asp Val Asp Phe Gly Trp Gly Lys Pro Glu Ser
    385                 390                 395 gtg agg agt ggt tcg aac aat agg ttt gat gga atg gtg tat ttg tac      1308
Val Arg Ser Gly Ser Asn Asn Arg Phe Asp Gly Met Val Tyr Leu Tyr
400                 405                 410 caa ggc aaa aat gga gga aga agc att gat gtg gag att agt ttg gaa      1356
Gln Gly Lys Asn Gly Gly Arg Ser Ile Asp Val Glu Ile Ser Leu Glu
415                 420                 425                 430 gca aat gct atg gag agg ttg gag aaa gat aaa gag ttc ctc atg gaa      1404
Ala Asn Ala Met Glu Arg Leu Glu Lys Asp Lys Glu Phe Leu Met Glu
                435                 440                 445 act gct taatttgctt agcttggact caactggcta cactttattt atgagctgct      1460
Thr Ala atgactcaca tgcatgtatg tttatttttt ttggagggt tctttccttt tattgttttc      1520
tatgtttttt ctttcttgta cgttatgaag agaaaccgag tataaaggaa taatgttttc      1580
agttattaaa aaaaaaaaaa aaaaa                                             1605

<210> SEQ ID NO 4
<211> LENGTH: 1479
<212> TYPE: DNA
<213> ORGANISM: Perilla ocimoides
<220> FEATURE:
<221> NAME/KEY: CDS
<222> LOCATION: (3)..(1340)

<400> SEQUENCE: 4 cc gtg atc gaa acg tgt aga gtt ggg ccg ccg ccg gac tcg gtg gcg         47
   Val Ile Glu Thr Cys Arg Val Gly Pro Pro Pro Asp Ser Val Ala
   1               5                  10                  15 gag caa tcg gtg ccg ctc aca ttc ttc gac atg acg tgg ctg cat ttt        95
Glu Gln Ser Val Pro Leu Thr Phe Phe Asp Met Thr Trp Leu His Phe
             20                  25                  30 cat ccc atg ctt cag ctc ctc ttc tac gaa ttc cct tgt tcc aag caa       143
His Pro Met Leu Gln Leu Leu Phe Tyr Glu Phe Pro Cys Ser Lys Gln
         35                  40                  45 cat ttt tca gaa tcc atc gtt cca aaa ctc aaa caa tct ctc tct aaa       191
His Phe Ser Glu Ser Ile Val Pro Lys Leu Lys Gln Ser Leu Ser Lys
     50                  55                  60 act ctc ata cac ttc ttc cct ctc tca tgc aat tta atc tac cct tca       239
Thr Leu Ile His Phe Phe Pro Leu Ser Cys Asn Leu Ile Tyr Pro Ser
 65                  70                  75 tcc ccg gag aaa atg ccg gag ttt cgg tat cta tcc ggg gac tcg gtt       287
Ser Pro Glu Lys Met Pro Glu Phe Arg Tyr Leu Ser Gly Asp Ser Val
 80                  85                  90                  95 tct ttc acc atc gca gaa tct agc gac gac ttc gat gat ctc gtc gga       335
Ser Phe Thr Ile Ala Glu Ser Ser Asp Asp Phe Asp Asp Leu Val Gly
                100                 105                 110 aat cgt cca gaa tct ccc gtt agg ctc tac aac ttt gtc cct aaa ttg       383
Asn Arg Pro Glu Ser Pro Val Arg Leu Tyr Asn Phe Val Pro Lys Leu
            115                 120                 125 ccg ccc att gtc gaa gaa tcc gat aga aaa ctc ttc caa gtt ttc gcc       431
Pro Pro Ile Val Glu Glu Ser Asp Arg Lys Leu Phe Gln Val Phe Ala
```

-continued

```
              130                 135                 140
gtg cag gtg act ctt ttc cca ggc cga ggc gtc ggt att gga ata gca       479
Val Gln Val Thr Leu Phe Pro Gly Arg Gly Val Gly Ile Gly Ile Ala
    145                 150                 155 acg cat cac acc gtt agc gac gcc ccg tcg ttt ctc gcg ttt ata acg       527
Thr His His Thr Val Ser Asp Ala Pro Ser Phe Leu Ala Phe Ile Thr
160                 165                 170                 175 gct tgg tct tca atg agc aaa cac att gaa aat gaa gat gaa gat gaa       575
Ala Trp Ser Ser Met Ser Lys His Ile Glu Asn Glu Asp Glu Asp Glu
                180                 185                 190 gaa ttt aaa tct ttg cca gtt ttc gat aga tcc gtc ata aaa tat ccg       623
Glu Phe Lys Ser Leu Pro Val Phe Asp Arg Ser Val Ile Lys Tyr Pro
        195                 200                 205 acg aaa ttt gac tcc att tat tgg aga aac gcg cta aaa ttt cct ttg       671
Thr Lys Phe Asp Ser Ile Tyr Trp Arg Asn Ala Leu Lys Phe Pro Leu
            210                 215                 220 caa tct cgt cat ccc tca tta ccg acg gac cgc att cga acc acg ttc       719
Gln Ser Arg His Pro Ser Leu Pro Thr Asp Arg Ile Arg Thr Thr Phe
225                 230                 235 gtt ttc acc caa tcc aaa att aag aaa ttg aag ggt tgg att cag tcc       767
Val Phe Thr Gln Ser Lys Ile Lys Lys Leu Lys Gly Trp Ile Gln Ser
240                 245                 250                 255 aga gtt cca agt tta gtc cat ctc tca tct ttt gta gcg att gca gct       815
Arg Val Pro Ser Leu Val His Leu Ser Ser Phe Val Ala Ile Ala Ala
            260                 265                 270 tat atg tgg gct ggc ata acg aaa tca ttc aca gca gat gaa gac caa       863
Tyr Met Trp Ala Gly Ile Thr Lys Ser Phe Thr Ala Asp Glu Asp Gln
            275                 280                 285 gac aac gag gat gca ttt ttc ttg att ccg gtc gat cta agg cca cga       911
Asp Asn Glu Asp Ala Phe Phe Leu Ile Pro Val Asp Leu Arg Pro Arg
            290                 295                 300 tta gat ccg ccg gtt cct gaa aat tac ttc ggg aac tgc tta tcg tac       959
Leu Asp Pro Pro Val Pro Glu Asn Tyr Phe Gly Asn Cys Leu Ser Tyr
305                 310                 315 gcg ctg ccg aga atg cgg cgg cga gag ctg gtg gga gag aaa ggg gtg      1007
Ala Leu Pro Arg Met Arg Arg Arg Glu Leu Val Gly Glu Lys Gly Val
320                 325                 330                 335 ttt ctg gca gct gag gta atc gcg gcg gag ata aaa aaa agg atc aac      1055
Phe Leu Ala Ala Glu Val Ile Ala Ala Glu Ile Lys Lys Arg Ile Asn
            340                 345                 350 gac aag aga ata tta gaa acg gtg gag aaa tgg tcg ccg gag att cgt      1103
Asp Lys Arg Ile Leu Glu Thr Val Glu Lys Trp Ser Pro Glu Ile Arg
            355                 360                 365 aaa gcg ttg cag aaa tca tat ttt tcg gtg gca gga tcg agc aag cta      1151
Lys Ala Leu Gln Lys Ser Tyr Phe Ser Val Ala Gly Ser Ser Lys Leu
        370                 375                 380 gat ctt tac ggt gca gat ttt gga tgg ggg aag gcg aga aag caa gaa      1199
Asp Leu Tyr Gly Ala Asp Phe Gly Trp Gly Lys Ala Arg Lys Gln Glu
385                 390                 395 ata ttg tcg att gat ggg gag aaa tat gca atg acg ctt tgt aaa gcc      1247
Ile Leu Ser Ile Asp Gly Glu Lys Tyr Ala Met Thr Leu Cys Lys Ala
400                 405                 410                 415 agg gat ttc gaa gga gga ttg gag gtt tgc ttg tct ttg cct aag gac      1295
Arg Asp Phe Glu Gly Gly Leu Glu Val Cys Leu Ser Leu Pro Lys Asp
                420                 425                 430 aaa atg gat gct ttt gct gct tat ttt tca ctg gga att aat ggt          1340
Lys Met Asp Ala Phe Ala Ala Tyr Phe Ser Leu Gly Ile Asn Gly
                435                 440                 445 taataaatgt atgtaattaa actaatatta ttatgtaaca attaattaag tgttgagtaa    1400
```

-continued

```
cgtgaagaat aatccctatt atatatttat gatttggttc aaataaagtg taaagcctct    1460
tgaaaaaaaa aaaaaaaaa                                                 1479

<210> SEQ ID NO 5
<211> LENGTH: 1508
<212> TYPE: DNA
<213> ORGANISM: Senecio cruentus
<220> FEATURE:
<221> NAME/KEY: CDS
<222> LOCATION: (3)..(1364)

<400> SEQUENCE: 5 tg aac att ctc gaa cat gcc cga ata tcg gcc ccc tcg ggc acc atc         47
   Asn Ile Leu Glu His Ala Arg Ile Ser Ala Pro Ser Gly Thr Ile
    1               5                  10                  15 ggc cat cgc tcg tta tct ctt act ttc ttc gac att act tgg cta ctc        95
Gly His Arg Ser Leu Ser Leu Thr Phe Phe Asp Ile Thr Trp Leu Leu
             20                  25                  30 ttc cct ccg gtc cac cat ctt ttc ttc tat gac ttt cca cat tct aaa       143
Phe Pro Pro Val His His Leu Phe Phe Tyr Asp Phe Pro His Ser Lys
         35                  40                  45 tcc cat ttc atg gac act att gtt ccc agg cta aaa caa tct tta tcg       191
Ser His Phe Met Asp Thr Ile Val Pro Arg Leu Lys Gln Ser Leu Ser
     50                  55                  60 gtc act ctt caa cat ttt ttc ccg ttt gct agt aat ttg att gta ttt       239
Val Thr Leu Gln His Phe Phe Pro Phe Ala Ser Asn Leu Ile Val Phe
 65                  70                  75 cct aac act gat ggt tcg ggt ttt aat aaa aaa cca gaa ata aaa cac       287
Pro Asn Thr Asp Gly Ser Gly Phe Asn Lys Lys Pro Glu Ile Lys His
 80                  85                  90                  95 gtt gaa ggt gat tct gtt gtg gtt act ttt gca gaa tgt tgt ctt gac       335
Val Glu Gly Asp Ser Val Val Val Thr Phe Ala Glu Cys Cys Leu Asp
                100                 105                 110 ttt aat aat ttg aca gga aat cat cct cga aaa tgt gaa aac ttt tat       383
Phe Asn Asn Leu Thr Gly Asn His Pro Arg Lys Cys Glu Asn Phe Tyr
            115                 120                 125 cca ctt gta cct tca ttg gga aat gca atc aaa tta tgt gat tgc gtc       431
Pro Leu Val Pro Ser Leu Gly Asn Ala Ile Lys Leu Cys Asp Cys Val
        130                 135                 140 acg gtc cca ctt ttt tca ctt caa gtg acg ttt ttt ccg ggc tcg ggt       479
Thr Val Pro Leu Phe Ser Leu Gln Val Thr Phe Phe Pro Gly Ser Gly
    145                 150                 155 ata tca cta gga atg acg aat cat cat agc ctt ggt gac gct agc acg       527
Ile Ser Leu Gly Met Thr Asn His His Ser Leu Gly Asp Ala Ser Thr
160                 165                 170                 175 cgg ttc aac ttt ttg aaa ggg tgg act tcg att att caa tct ggt gta       575
Arg Phe Asn Phe Leu Lys Gly Trp Thr Ser Ile Ile Gln Ser Gly Val
                180                 185                 190 gat cgg tct ttt tta acg aaa gga tct cca ccg gtt ttt gat aga ttg       623
Asp Arg Ser Phe Leu Thr Lys Gly Ser Pro Pro Val Phe Asp Arg Leu
            195                 200                 205 att aac atc cca cat tta gat gaa aat aag ttg aga cat aca agg ctc       671
Ile Asn Ile Pro His Leu Asp Glu Asn Lys Leu Arg His Thr Arg Leu
        210                 215                 220 gaa agt ttt tat aaa cct tcg agc ctt gtt ggt ccc act gat aaa gtt       719
Glu Ser Phe Tyr Lys Pro Ser Ser Leu Val Gly Pro Thr Asp Lys Val
    225                 230                 235 cgg tca acg ttt gtg ttg acc cga act aat atc aat cta cta aag aaa       767
Arg Ser Thr Phe Val Leu Thr Arg Thr Asn Ile Asn Leu Leu Lys Lys
240                 245                 250                 255
```

-continued

```
aag gtc tta acc caa gtg cca aac ttg gag tac atg tca tct ttt acg      815
Lys Val Leu Thr Gln Val Pro Asn Leu Glu Tyr Met Ser Ser Phe Thr
            260                 265                 270 gta act tgt ggt tat ata tgg agt tgc ata gcg aaa tca ctc gta aaa      863
Val Thr Cys Gly Tyr Ile Trp Ser Cys Ile Ala Lys Ser Leu Val Lys
    275                 280                 285 ata gga gaa aga aag ggc gaa gac gag tta gaa cag ttc ata atc acc      911
Ile Gly Glu Arg Lys Gly Glu Asp Glu Leu Glu Gln Phe Ile Ile Thr
290                 295                 300 att gat tgt cga tct cgt ctt gat cca cca att ccc aca gcc tac ttt      959
Ile Asp Cys Arg Ser Arg Leu Asp Pro Pro Ile Pro Thr Ala Tyr Phe
    305                 310                 315 ggt aac tgt ggt gca cca tgt gtc ccg acc tta aaa aat gtc gtt ttg     1007
Gly Asn Cys Gly Ala Pro Cys Val Pro Thr Leu Lys Asn Val Val Leu
320                 325                 330                 335 act acg gaa aat ggg tat gca ctt ggt gct aaa gta att gga gag tct     1055
Thr Thr Glu Asn Gly Tyr Ala Leu Gly Ala Lys Val Ile Gly Glu Ser
            340                 345                 350 ata tgc aaa atg ata tat aat aag gac gga atc ttg aaa gat gcc gcg     1103
Ile Cys Lys Met Ile Tyr Asn Lys Asp Gly Ile Leu Lys Asp Ala Ala
    355                 360                 365 aga tgg cat gaa cct ttc atg atc ccg gct agg aag att ggt gtt gct     1151
Arg Trp His Glu Pro Phe Met Ile Pro Ala Arg Lys Ile Gly Val Ala
370                 375                 380 ggt aca cct aag ctc aac ttg tac gac ttt gat ttt ggg tgg ggg aag     1199
Gly Thr Pro Lys Leu Asn Leu Tyr Asp Phe Asp Phe Gly Trp Gly Lys
    385                 390                 395 cgc ata aag tat gag act gtt tca ata gac tat aat acg tcg att tct     1247
Arg Ile Lys Tyr Glu Thr Val Ser Ile Asp Tyr Asn Thr Ser Ile Ser
400                 405                 410                 415 ata aat gca agc aaa aca tca gca caa gat ctt gaa att gga ttg agt     1295
Ile Asn Ala Ser Lys Thr Ser Ala Gln Asp Leu Glu Ile Gly Leu Ser
            420                 425                 430 cta ccg agt atg caa atg gag gcg ttt tct agc atc ttt gat gaa gga     1343
Leu Pro Ser Met Gln Met Glu Ala Phe Ser Ser Ile Phe Asp Glu Gly
    435                 440                 445 tta gag agt caa gtt tca ttg tagatcatcg tcccctttttt gtgtgcatca       1394
Leu Glu Ser Gln Val Ser Leu
            450 agtttctgtc gttttatga gttgccactg ttctattctt taagtatacc tttcgactat    1454 gttttgaaga tgcaacgata taaatgaaa aaaaaaaaa aaaaaaaaaa aaaa           1508
```

<210> SEQ ID NO 6
<211> LENGTH: 1521
<212> TYPE: DNA
<213> ORGANISM: Lavandula angustifolia
<220> FEATURE:
<221> NAME/KEY: CDS
<222> LOCATION: (3)..(1352)

<400> SEQUENCE: 6

```
tg acc acc ctc ctc gaa tcc tcc cga gtg gcg ccg cct cca ggc acg       47
   Thr Thr Leu Leu Glu Ser Ser Arg Val Ala Pro Pro Pro Gly Thr
     1               5                  10                  15 gtg gct gag cag tca ctc ccg ctc acc ttc ttc gac atg acg tgg ctg       95
Val Ala Glu Gln Ser Leu Pro Leu Thr Phe Phe Asp Met Thr Trp Leu
                20                  25                  30 cat ttc cac ccc atg ctt cag ctt ctc ttc tac gaa ctc ccc tgt tcc      143
His Phe His Pro Met Leu Gln Leu Leu Phe Tyr Glu Leu Pro Cys Ser
        35                  40                  45
```

-continued

| | |
|---|---|
| aaa ccc gcc ttc ctc gaa acc gtc gtt ccg aaa ctc aaa caa tcc tta<br>Lys Pro Ala Phe Leu Glu Thr Val Val Pro Lys Leu Lys Gln Ser Leu<br>50                        55                     60 | 191 |
| tct cta acc ctc aaa cac ttc ttc ccc ctt tca tgc aat cta atc tac<br>Ser Leu Thr Leu Lys His Phe Phe Pro Leu Ser Cys Asn Leu Ile Tyr<br>65                       70                     75 | 239 |
| cct cta tcg ccg gag aaa atg ccg gag ttc cgg tat cag aac ggt gac<br>Pro Leu Ser Pro Glu Lys Met Pro Glu Phe Arg Tyr Gln Asn Gly Asp<br>80                       85                     90                 95 | 287 |
| tcg gtt tct ttc acg att atg gag tct gtc gga gat cat ccg cat tcc<br>Ser Val Ser Phe Thr Ile Met Glu Ser Val Gly Asp His Pro His Ser<br>                      100                  105                110 | 335 |
| gct cat aaa tac tac tgc ttt gcc cct agc gac gat tat gaa gat ctc<br>Ala His Lys Tyr Tyr Cys Phe Ala Pro Ser Asp Asp Tyr Glu Asp Leu<br>                      115                  120                125 | 383 |
| cag ctg ccg ccg ata gtc gag gaa tct gat cgg aaa ttg ttt caa gtt<br>Gln Leu Pro Pro Ile Val Glu Glu Ser Asp Arg Lys Leu Phe Gln Val<br>                      130                  135                140 | 431 |
| tta gcc gtg caa gtg act ctg ttt ccc ggt cgc ggg gtg tgc atc gga<br>Leu Ala Val Gln Val Thr Leu Phe Pro Gly Arg Gly Val Cys Ile Gly<br>145                     150                  155 | 479 |
| ata acg acg cac cac acc gtt agc gat gct cca tcg ttt gta ggg ttt<br>Ile Thr Thr His His Thr Val Ser Asp Ala Pro Ser Phe Val Gly Phe<br>160                     165                  170                175 | 527 |
| atg aag agt tgg gct tcc atc act aaa ttc gga gga gat gat gaa ttc<br>Met Lys Ser Trp Ala Ser Ile Thr Lys Phe Gly Gly Asp Asp Glu Phe<br>                      180                  185                190 | 575 |
| ttg gac gga aaa ggt gaa tgt ttg ccg gtt ttc gac cga tcg ctc gtg<br>Leu Asp Gly Lys Gly Glu Cys Leu Pro Val Phe Asp Arg Ser Leu Val<br>                      195                  200                205 | 623 |
| aat tat ccg cct aaa ttg gac aca tat tta tgg aac aac gcg cag aaa<br>Asn Tyr Pro Pro Lys Leu Asp Thr Tyr Leu Trp Asn Asn Ala Gln Lys<br>                      210                  215                220 | 671 |
| cgt ccg ttg gaa tcg cag cat cca tct tta ccg acg gat cgg att cga<br>Arg Pro Leu Glu Ser Gln His Pro Ser Leu Pro Thr Asp Arg Ile Arg<br>225                     230                  235 | 719 |
| gct acc tac ctt ttc acc caa tct gaa att aag aaa ttg aag ggt ttg<br>Ala Thr Tyr Leu Phe Thr Gln Ser Glu Ile Lys Lys Leu Lys Gly Leu<br>240                     245                  250                255 | 767 |
| att cag aga aaa gcc cca aat gta gtt aat ctc tct tcc ttc gtc gcg<br>Ile Gln Arg Lys Ala Pro Asn Val Val Asn Leu Ser Ser Phe Val Ala<br>                      260                  265                270 | 815 |
| atc gca gct tat atc tgg acc ggc atc gcc aaa tcg gtc gga gat tac<br>Ile Ala Ala Tyr Ile Trp Thr Gly Ile Ala Lys Ser Val Gly Asp Tyr<br>                      275                  280                285 | 863 |
| aaa gac gtg gat gac gac aaa cgc gct ttc ttt tta att ccg atc gat<br>Lys Asp Val Asp Asp Asp Lys Arg Ala Phe Phe Leu Ile Pro Ile Asp<br>290                     295                  300 | 911 |
| tta agg ccg cgt ttg gat ccg ccg gct ccg ggg aac tac ttc gga aac<br>Leu Arg Pro Arg Leu Asp Pro Pro Ala Pro Gly Asn Tyr Phe Gly Asn<br>305                     310                  315 | 959 |
| tgt cta tcg ttt gcg atg gcg aag atc ctg cgg cgg gat ttg gtc gga<br>Cys Leu Ser Phe Ala Met Ala Lys Ile Leu Arg Arg Asp Leu Val Gly<br>320                     325                  330                335 | 1007 |
| gat gaa ggg gtg ttt cgg gca gct gag gcg atc gcg gcg gaa ata gag<br>Asp Glu Gly Val Phe Arg Ala Ala Glu Ala Ile Ala Ala Glu Ile Glu<br>                      340                  345                350 | 1055 |
| aag agg acg agc gac aag aag att cta gaa act gtg gag aac tgg ccg<br>Lys Arg Thr Ser Asp Lys Lys Ile Leu Glu Thr Val Glu Asn Trp Pro | 1103 |

-continued

```
                355                 360                 365
tct gag att cgc gaa gcc ttg caa aac tgt tat ttc tcg gtg gcg gga      1151
Ser Glu Ile Arg Glu Ala Leu Gln Asn Cys Tyr Phe Ser Val Ala Gly
        370                 375                 380 tcg agc agg ctt gat ctt tac ggc gcg gat ttt gga tgg ggt aag gcg      1199
Ser Ser Arg Leu Asp Leu Tyr Gly Ala Asp Phe Gly Trp Gly Lys Ala
385                 390                 395 gtg aag caa gag ata ctg tcg att gat gga gag aag ttt acg atg tcg      1247
Val Lys Gln Glu Ile Leu Ser Ile Asp Gly Glu Lys Phe Thr Met Ser
400                 405                 410                 415 ttg tgt aaa ccg agg gat gct gcc gga gga ttg gag gtt gga ttg tct      1295
Leu Cys Lys Pro Arg Asp Ala Ala Gly Gly Leu Glu Val Gly Leu Ser
                420                 425                 430 ttg cca aag gag gaa ttg caa gct ttt gat gat tat ttt gcg gag gga      1343
Leu Pro Lys Glu Glu Leu Gln Ala Phe Asp Asp Tyr Phe Ala Glu Gly
            435                 440                 445 ata aag ggt tgattaatca tttaatcatg tattatgaag ttggatgaaa              1392
Ile Lys Gly
        450 tcctctgttt catctctatt gtttaaacaa taattttttt ccattgaact tttttgagtc    1452 aataaaaaaa aaaaaaaaa aaaaaaatg aaaaaactca gttattttt tttttttttt      1512 tttttttt                                                             1521

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Phe Leu Gly Ile Thr Gly Ser Pro Lys
 1               5                  10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile His Met Asp Ala Phe Ala Lys
 1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Val Glu Ile Gly Val Ser Leu Pro Lys
 1               5                  10

<210> SEQ ID NO 10
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Ala Ser Leu Ser Leu Thr Leu Lys
 1               5

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Tyr Val Pro Leu Ser Gly Asn Leu Leu Met Pro Ile Lys
 1               5                  10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Arg Ala Thr Tyr Val Leu Ser Leu Ala Glu Ile Gln Lys
 1               5                  10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile His Met Asp Ala Phe Ala Lys
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Ile His Met Asp Ala Phe Ala Lys
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ile His Met Asp Ala Phe Ala
 1               5
```

```
<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)
<223> OTHER INFORMATION: a, c, g, t, unknown, or other

<400> SEQUENCE: 16
aarathcaya tggaygcntt ygc                                              23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctcgagtttt tttttttttt ttt                                              23

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ttcaccatgg agcaaatcca aatggt                                           26

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgagtcgccc tcatcac                                                     17

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aacagctatg accatg                                                      16

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

Asp Phe Gly Trp Gly Lys
  1               5

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: a, c, g, t, unknown, or other
<220> FEATURE:
<221> NAME/KEY: modified_base
<222> LOCATION: (15)
<223> OTHER INFORMATION: a, c, g, t, unknown, or other

<400> SEQUENCE: 22
gayttyggnt ggggnaa                                                  17

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tggcaactgt cttgcgtcat g                                             21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccatgtcagg tgtgaggttc aac                                           23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atcgtttcgc atgattgaac                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcagaagaac tcgtcaagaa                                               20

<210> SEQ ID NO 27

```
<211> LENGTH: 53
<212> TYPE: DNA
<213> ORGANISM: Artificial Sequence
<220> FEATURE:
<223> OTHER INFORMATION: Description of Artificial Sequence: Synthetic
      nucleotide
<220> FEATURE:
<221> NAME/KEY: CDS
<222> LOCATION: (12)..(53)

<400> SEQUENCE: 27
gggatccaac a atg gag caa atc caa atg gtg gcc gtg atc gaa acg tgt        50
            Met Glu Gln Ile Gln Met Val Ala Val Ile Glu Thr Cys
             1               5                  10 aga                                                                     53
Arg

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtaaaacgac ggccat                                                       16

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      nucleotide
<220> FEATURE:
<221> NAME/KEY: CDS
<222> LOCATION: (12)..(44)

<400> SEQUENCE: 29
gggatccaac a atg gag caa atc caa atg gtg aac att ctc gaa c              45
            Met Glu Gln Ile Gln Met Val Asn Ile Leu Glu
             1               5                  10

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctcggaggaa ttcggcacga c                                                 21

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      nucleotide
<220> FEATURE:
<221> NAME/KEY: CDS
<222> LOCATION: (18)..(35)

<400> SEQUENCE: 31
agtcggatcc aacaatg acc acc ctc ctc gaa tcc                              35
                   Thr Thr Leu Leu Glu Ser
```

<210> SEQ ID NO 32
<211> LENGTH: 469
<212> TYPE: PRT
<213> ORGANISM: Gentiana triflora

<400> SEQUENCE: 32

```
Met Glu Gln Ile Gln Met Val Lys Val Leu Glu Lys Cys Gln Val Thr
  1               5                  10                  15
Pro Pro Ser Asp Thr Thr Asp Val Glu Leu Ser Leu Pro Val Thr Phe
             20                  25                  30
Phe Asp Ile Pro Trp Leu His Leu Asn Lys Met Gln Ser Leu Leu Phe
         35                  40                  45
Tyr Asp Phe Pro Tyr Pro Arg Thr His Phe Leu Asp Thr Val Ile Pro
     50                  55                  60
Asn Leu Lys Ala Ser Leu Ser Leu Thr Leu Lys His Tyr Val Pro Leu
 65                  70                  75                  80
Ser Gly Asn Leu Leu Met Pro Ile Lys Ser Gly Glu Met Pro Lys Phe
                 85                  90                  95
Gln Tyr Ser Arg Asp Glu Gly Asp Ser Ile Thr Leu Ile Val Ala Glu
            100                 105                 110
Ser Asp Gln Asp Phe Asp Tyr Leu Lys Gly His Gln Leu Val Asp Ser
        115                 120                 125
Asn Asp Leu His Gly Leu Phe Tyr Val Met Pro Arg Val Ile Arg Thr
    130                 135                 140
Met Gln Asp Tyr Lys Val Ile Pro Leu Val Ala Val Gln Val Thr Val
145                 150                 155                 160
Phe Pro Asn Arg Gly Ile Ala Val Ala Leu Thr Ala His His Ser Ile
                165                 170                 175
Ala Asp Ala Lys Ser Phe Val Met Phe Ile Asn Ala Trp Ala Tyr Ile
            180                 185                 190
Asn Lys Phe Gly Lys Asp Ala Asp Leu Leu Ser Ala Asn Leu Leu Pro
        195                 200                 205
Ser Phe Asp Arg Ser Ile Ile Lys Asp Leu Tyr Gly Leu Glu Glu Thr
    210                 215                 220
Phe Trp Asn Glu Met Gln Asp Val Leu Glu Met Phe Ser Arg Phe Gly
225                 230                 235                 240
Ser Lys Pro Pro Arg Phe Asn Lys Val Arg Ala Thr Tyr Val Leu Ser
                245                 250                 255
Leu Ala Glu Ile Gln Lys Leu Lys Asn Lys Val Leu Asn Leu Arg Gly
            260                 265                 270
Ser Glu Pro Thr Ile Arg Val Thr Thr Phe Thr Met Thr Cys Gly Tyr
        275                 280                 285
Val Trp Thr Cys Met Val Lys Ser Lys Asp Asp Val Val Ser Glu Glu
    290                 295                 300
Ser Ser Asn Asp Glu Asn Glu Leu Glu Tyr Phe Ser Phe Thr Ala Asp
305                 310                 315                 320
Cys Arg Gly Leu Leu Thr Pro Pro Cys Pro Pro Asn Tyr Phe Gly Asn
                325                 330                 335
Cys Leu Ala Ser Cys Val Ala Lys Ala Thr His Lys Glu Leu Val Gly
            340                 345                 350
Asp Lys Gly Leu Leu Val Ala Val Ala Ala Ile Gly Glu Ala Ile Glu
        355                 360                 365
```

```
Lys Arg Leu His Asn Glu Lys Gly Val Leu Ala Asp Ala Lys Thr Trp
    370                 375                 380
Leu Ser Glu Ser Asn Gly Ile Pro Ser Lys Arg Phe Leu Gly Ile Thr
385                 390                 395                 400
Gly Ser Pro Lys Phe Asp Ser Tyr Gly Val Asp Phe Gly Trp Gly Lys
                405                 410                 415
Pro Ala Lys Phe Asp Ile Thr Ser Val Asp Tyr Ala Glu Leu Ile Tyr
                420                 425                 430
Val Ile Gln Ser Arg Asp Phe Glu Lys Gly Val Glu Ile Gly Val Ser
                435                 440                 445
Leu Pro Lys Ile His Met Asp Ala Phe Ala Lys Ile Phe Glu Glu Gly
450                 455                 460
Phe Cys Ser Leu Ser
465

<210> SEQ ID NO 33
<211> LENGTH: 479
<212> TYPE: PRT
<213> ORGANISM: Gentiana triflora

<400> SEQUENCE: 33

Met Ala Gly Asn Ser Glu Asp Ile Lys Val Leu Glu Lys Cys Arg Val
1               5                   10                  15
Ala Pro Pro Asp Ala Val Ala Glu Phe Thr Val Pro Leu Ser Phe
                20                  25                  30
Phe Asp Met Arg Trp Leu Ile Ser Asp Ala Glu His His Leu His Phe
            35                  40                  45
Tyr Arg Phe Arg His Pro Cys Pro Asn Ser Lys Phe Ile Ile Ser Ser
        50                  55                  60
Ile Lys Ser Ser Leu Ser Leu Val Leu Lys His Phe Leu Pro Leu Ala
65                  70                  75                  80
Gly Asn Leu Ile Trp Pro Val Asp Ser Ser Asp Arg Met Pro Glu Leu
                85                  90                  95
Arg Tyr Lys Lys Gly Asp Ser Val Ser Leu Thr Ile Ala Glu Ser Ser
                100                 105                 110
Met Asp Phe Asp Tyr Leu Ala Gly Asp His Gln Arg Asp Ser Tyr Lys
            115                 120                 125
Phe Asn Asp Leu Ile Pro Gln Leu Pro Glu Pro Ile Val Thr Ser Gly
130                 135                 140
Asp Glu Val Leu Pro Leu Phe Ala Leu Gln Val Thr Val Phe Ser Asn
145                 150                 155                 160
Thr Gly Ile Cys Ile Gly Arg Asn Leu His Gln Val Leu Gly Asp Ala
                165                 170                 175
Ser Ser Phe Leu His Phe Asn Lys Leu Trp Val Leu Val Asp Lys Ser
            180                 185                 190
Asn Gly Asp Ser Leu Lys Phe Leu Pro Leu Ser Ser Leu Pro Met Tyr
        195                 200                 205
Asp Arg Ser Val Val Gln Asp Pro Phe His Ile Arg Arg Lys Ile Tyr
    210                 215                 220
Asn Glu Arg Lys Leu Leu Lys Ser Gln Gly Thr Pro Thr Val Leu Asn
225                 230                 235                 240
Pro Ala Ile Ser Lys Asp Glu Val Arg Ala Thr Phe Ile Leu His Pro
                245                 250                 255
Ile Asp Ile Met Lys Leu Lys Lys Phe Ile Ser Ser Lys Asn Arg Asn
            260                 265                 270
```

-continued

```
Leu Thr Gly Ser Ser Asn Tyr Asn Leu Ser Thr Phe Thr Val Thr Ser
            275                 280                 285
Ala Leu Ile Trp Thr Cys Leu Ser Lys Ser Leu Asp Thr Val Val Arg
        290                 295                 300
Glu Lys Val Glu Glu Asp Lys His Ala Ala Asn Leu Cys Ala Phe Ile
305                 310                 315                 320
Asn Cys Arg Gln Arg Phe Ala Pro Pro Ile Pro Gln Asn Tyr Phe Gly
                325                 330                 335
Asn Cys Ile Val Pro Cys Met Val Gly Ser Thr His Glu Gln Leu Val
            340                 345                 350
Gly Asn Glu Gly Leu Ser Val Ala Ala Thr Ala Ile Gly Asp Ala Ile
        355                 360                 365
His Lys Arg Leu His Asp Tyr Glu Gly Ile Leu Arg Gly Asp Trp Ile
370                 375                 380
Ser Pro Pro Arg Ser Thr Ser Ala Ala Pro Arg Ser Thr Leu Ile Tyr
385                 390                 395                 400
Val Val Gly Ser Ala Gln Arg Asn Val His Asp Phe Asp Ala Asp Phe
                405                 410                 415
Gly Trp Gly Lys Leu Glu Lys His Glu Ser Val Ser Thr Asn Pro Ser
            420                 425                 430
Ala Thr Leu Ile Leu Ile Ser Arg Ser Arg Arg Phe Lys Gly Ala Leu
        435                 440                 445
Glu Leu Gly Ile Ser Leu Pro Lys Asn Arg Met Asp Ala Phe Ala Thr
450                 455                 460
Ile Phe Thr Asn Phe Ile Asn Ser Leu His Val Arg Ser Pro Leu
465                 470                 475
```

<210> SEQ ID NO 34
<211> LENGTH: 448
<212> TYPE: PRT
<213> ORGANISM: Petunia hybrida

<400> SEQUENCE: 34

```
Met Ala Gly Glu Val Ala Lys Gln Glu Val Thr Lys Val Lys Val Leu
1               5                   10                  15
Lys Lys Thr Asn Val Lys Pro His Lys Pro Leu Gly Lys Lys Glu Cys
            20                  25                  30
Gln Leu Val Thr Phe Asp Leu Pro Tyr Leu Ala Phe Tyr Tyr Asn Gln
        35                  40                  45
Lys Phe Leu Ile Tyr Lys Gly Ala Glu Asn Phe Asp Glu Thr Val Glu
    50                  55                  60
Lys Ile Lys Asp Gly Leu Ala Leu Val Leu Asp Phe Tyr Gln Leu
65                  70                  75              80
Ala Gly Lys Leu Gly Lys Asp Glu Glu Gly Val Phe Arg Val Glu Tyr
                85                  90                  95
Asp Asp Asp Met Asp Gly Val Glu Val Thr Val Ala Val Ala Glu Glu
            100                 105                 110
Ile Glu Val Ala Asp Leu Thr Asp Glu Glu Gly Thr Thr Lys Leu Gln
        115                 120                 125
Asp Leu Ile Pro Cys Asn Lys Ile Leu Asn Leu Glu Gly Leu His Arg
    130                 135                 140
Pro Leu Leu Ala Val Gln Leu Thr Lys Leu Lys Asp Gly Leu Thr Met
145                 150                 155                 160
Gly Leu Ala Phe Asn His Ala Val Leu Asp Gly Thr Ser Thr Trp His
```

-continued

```
                    165                 170                 175
Phe Met Thr Ser Trp Ser Glu Leu Cys Cys Gly Ser Thr Ser Ile Ser
                180                 185                 190
Val Pro Pro Phe Leu Glu Arg Thr Lys Ala Arg Asn Thr Arg Val Lys
            195                 200                 205
Leu Asn Leu Ser Gln Pro Ser Asp Ala Pro Glu His Ala Lys Ser Ala
        210                 215                 220
Thr Asn Gly Asp Val Pro Ala Asn Val Asp Pro Leu Arg Glu Arg
225                 230                 235                 240
Val Phe Lys Phe Ser Glu Leu Ala Ile Asp Lys Ile Lys Ser Thr Val
                245                 250                 255
Asn Ala Asn Ser Gly Glu Thr Pro Phe Ser Thr Phe Gln Ser Leu Ser
                260                 265                 270
Ala His Val Trp Leu Ala Val Thr Arg Ala Arg Gln Leu Lys Pro Glu
            275                 280                 285
Asp Tyr Thr Val Tyr Thr Val Phe Ala Asp Cys Arg Lys Arg Val Asp
        290                 295                 300
Pro Pro Met Pro Glu Ser Tyr Phe Gly Asn Leu Ile Gln Ala Ile Phe
305                 310                 315                 320
Thr Val Thr Ala Ala Gly Leu Leu Ala Ser Pro Ile Glu Phe Ala
                325                 330                 335
Gly Gly Met Ile Gln Gln Ala Ile Val Lys His Asp Ala Lys Ala Ile
                340                 345                 350
Asp Glu Arg Asn Lys Glu Trp Glu Ser Asn Pro Lys Ile Phe Gln Tyr
            355                 360                 365
Lys Asp Ala Gly Val Asn Cys Val Ala Val Gly Ser Ser Pro Arg Phe
        370                 375                 380
Lys Val Tyr Asp Val Asp Phe Gly Trp Gly Lys Pro Glu Ser Val Arg
385                 390                 395                 400
Ser Gly Ser Asn Asn Arg Phe Asp Gly Met Val Tyr Leu Tyr Gln Gly
                405                 410                 415
Lys Asn Gly Gly Arg Ser Ile Asp Val Glu Ile Ser Leu Glu Ala Asn
                420                 425                 430
Ala Met Glu Arg Leu Glu Lys Asp Lys Glu Phe Leu Met Glu Thr Ala
            435                 440                 445
```

<210> SEQ ID NO 35
<211> LENGTH: 446
<212> TYPE: PRT
<213> ORGANISM: Perilla ocimoides

<400> SEQUENCE: 35

```
Val Ile Glu Thr Cys Arg Val Gly Pro Pro Asp Ser Val Ala Glu
  1               5                  10                  15
Gln Ser Val Pro Leu Thr Phe Phe Asp Met Thr Trp Leu His Phe His
                20                  25                  30
Pro Met Leu Gln Leu Leu Phe Tyr Glu Phe Pro Cys Ser Lys Gln His
            35                  40                  45
Phe Ser Glu Ser Ile Val Pro Lys Leu Lys Gln Ser Leu Ser Lys Thr
        50                  55                  60
Leu Ile His Phe Phe Pro Leu Ser Cys Asn Leu Ile Tyr Pro Ser Ser
65                  70                  75                  80
Pro Glu Lys Met Pro Glu Phe Arg Tyr Leu Ser Gly Asp Ser Val Ser
                85                  90                  95
```

```
Phe Thr Ile Ala Glu Ser Ser Asp Asp Phe Asp Asp Leu Val Gly Asn
            100                 105                 110

Arg Pro Glu Ser Pro Val Arg Leu Tyr Asn Phe Val Pro Lys Leu Pro
        115                 120                 125

Pro Ile Val Glu Glu Ser Asp Arg Lys Leu Phe Gln Val Phe Ala Val
    130                 135                 140

Gln Val Thr Leu Phe Pro Gly Arg Gly Val Gly Ile Gly Ile Ala Thr
145                 150                 155                 160

His His Thr Val Ser Asp Ala Pro Ser Phe Leu Ala Phe Ile Thr Ala
                165                 170                 175

Trp Ser Ser Met Ser Lys His Ile Glu Asn Glu Asp Glu Asp Glu Glu
                180                 185                 190

Phe Lys Ser Leu Pro Val Phe Asp Arg Ser Val Ile Lys Tyr Pro Thr
            195                 200                 205

Lys Phe Asp Ser Ile Tyr Trp Arg Asn Ala Leu Lys Phe Pro Leu Gln
        210                 215                 220

Ser Arg His Pro Ser Leu Pro Thr Asp Arg Ile Arg Thr Thr Phe Val
225                 230                 235                 240

Phe Thr Gln Ser Lys Ile Lys Lys Leu Lys Gly Trp Ile Gln Ser Arg
                245                 250                 255

Val Pro Ser Leu Val His Leu Ser Ser Phe Val Ala Ile Ala Ala Tyr
            260                 265                 270

Met Trp Ala Gly Ile Thr Lys Ser Phe Thr Ala Asp Glu Asp Gln Asp
            275                 280                 285

Asn Glu Asp Ala Phe Phe Leu Ile Pro Val Asp Leu Arg Pro Arg Leu
        290                 295                 300

Asp Pro Pro Val Pro Glu Asn Tyr Phe Gly Asn Cys Leu Ser Tyr Ala
305                 310                 315                 320

Leu Pro Arg Met Arg Arg Glu Leu Val Gly Glu Lys Gly Val Phe
                325                 330                 335

Leu Ala Ala Glu Val Ile Ala Ala Glu Ile Lys Lys Arg Ile Asn Asp
            340                 345                 350

Lys Arg Ile Leu Glu Thr Val Glu Lys Trp Ser Pro Glu Ile Arg Lys
        355                 360                 365

Ala Leu Gln Lys Ser Tyr Phe Ser Val Ala Gly Ser Ser Lys Leu Asp
        370                 375                 380

Leu Tyr Gly Ala Asp Phe Gly Trp Gly Lys Ala Arg Lys Gln Glu Ile
385                 390                 395                 400

Leu Ser Ile Asp Gly Glu Lys Tyr Ala Met Thr Leu Cys Lys Ala Arg
                405                 410                 415

Asp Phe Glu Gly Gly Leu Glu Val Cys Leu Ser Leu Pro Lys Asp Lys
            420                 425                 430

Met Asp Ala Phe Ala Ala Tyr Phe Ser Leu Gly Ile Asn Gly
            435                 440                 445

<210> SEQ ID NO 36
<211> LENGTH: 454
<212> TYPE: PRT
<213> ORGANISM: Senecio cruentus

<400> SEQUENCE: 36

Asn Ile Leu Glu His Ala Arg Ile Ser Ala Pro Ser Gly Thr Ile Gly
 1               5                  10                  15

His Arg Ser Leu Ser Leu Thr Phe Phe Asp Ile Thr Trp Leu Leu Phe
            20                  25                  30
```

```
Pro Pro Val His His Leu Phe Phe Tyr Asp Phe Pro His Ser Lys Ser
        35                  40                  45

His Phe Met Asp Thr Ile Val Pro Arg Leu Lys Gln Ser Leu Ser Val
 50                  55                  60

Thr Leu Gln His Phe Phe Pro Phe Ala Ser Asn Leu Ile Val Phe Pro
 65                  70                  75                  80

Asn Thr Asp Gly Ser Gly Phe Asn Lys Lys Pro Glu Ile Lys His Val
                 85                  90                  95

Glu Gly Asp Ser Val Val Thr Phe Ala Glu Cys Cys Leu Asp Phe
                100                 105                 110

Asn Asn Leu Thr Gly Asn His Pro Arg Lys Cys Glu Asn Phe Tyr Pro
            115                 120                 125

Leu Val Pro Ser Leu Gly Asn Ala Ile Lys Leu Cys Asp Cys Val Thr
        130                 135                 140

Val Pro Leu Phe Ser Leu Gln Val Thr Phe Phe Pro Gly Ser Gly Ile
145                 150                 155                 160

Ser Leu Gly Met Thr Asn His His Ser Leu Gly Asp Ala Ser Thr Arg
                165                 170                 175

Phe Asn Phe Leu Lys Gly Trp Thr Ser Ile Ile Gln Ser Gly Val Asp
            180                 185                 190

Arg Ser Phe Leu Thr Lys Gly Ser Pro Pro Val Phe Asp Arg Leu Ile
        195                 200                 205

Asn Ile Pro His Leu Asp Glu Asn Lys Leu Arg His Thr Arg Leu Glu
    210                 215                 220

Ser Phe Tyr Lys Pro Ser Ser Leu Val Gly Pro Thr Asp Lys Val Arg
225                 230                 235                 240

Ser Thr Phe Val Leu Thr Arg Thr Asn Ile Asn Leu Leu Lys Lys Lys
                245                 250                 255

Val Leu Thr Gln Val Pro Asn Leu Glu Tyr Met Ser Ser Phe Thr Val
            260                 265                 270

Thr Cys Gly Tyr Ile Trp Ser Cys Ile Ala Lys Ser Leu Val Lys Ile
        275                 280                 285

Gly Glu Arg Lys Gly Glu Asp Glu Leu Glu Gln Phe Ile Ile Thr Ile
290                 295                 300

Asp Cys Arg Ser Arg Leu Asp Pro Pro Ile Pro Thr Ala Tyr Phe Gly
305                 310                 315                 320

Asn Cys Gly Ala Pro Cys Val Pro Thr Leu Lys Asn Val Val Leu Thr
                325                 330                 335

Thr Glu Asn Gly Tyr Ala Leu Gly Ala Lys Val Ile Gly Glu Ser Ile
            340                 345                 350

Cys Lys Met Ile Tyr Asn Lys Asp Gly Ile Leu Lys Asp Ala Ala Arg
        355                 360                 365

Trp His Glu Pro Phe Met Ile Pro Ala Arg Lys Ile Gly Val Ala Gly
    370                 375                 380

Thr Pro Lys Leu Asn Leu Tyr Asp Phe Asp Phe Gly Trp Gly Lys Arg
385                 390                 395                 400

Ile Lys Tyr Glu Thr Val Ser Ile Asp Tyr Asn Thr Ser Ile Ser Ile
                405                 410                 415

Asn Ala Ser Lys Thr Ser Ala Gln Asp Leu Glu Ile Gly Leu Ser Leu
            420                 425                 430

Pro Ser Met Gln Met Glu Ala Phe Ser Ser Ile Phe Asp Glu Gly Leu
        435                 440                 445
```

Glu Ser Gln Val Ser Leu
    450

<210> SEQ ID NO 37
<211> LENGTH: 450
<212> TYPE: PRT
<213> ORGANISM: Lavandula angustifolia

<400> SEQUENCE: 37

Thr Thr Leu Leu Glu Ser Ser Arg Val Ala Pro Pro Gly Thr Val
  1               5                  10                  15

Ala Glu Gln Ser Leu Pro Leu Thr Phe Phe Asp Met Thr Trp Leu His
             20                  25                  30

Phe His Pro Met Leu Gln Leu Leu Phe Tyr Glu Leu Pro Cys Ser Lys
         35                  40                  45

Pro Ala Phe Leu Glu Thr Val Val Pro Lys Leu Lys Gln Ser Leu Ser
     50                  55                  60

Leu Thr Leu Lys His Phe Phe Pro Leu Ser Cys Asn Leu Ile Tyr Pro
 65                  70                  75                  80

Leu Ser Pro Glu Lys Met Pro Glu Phe Arg Tyr Gln Asn Gly Asp Ser
                 85                  90                  95

Val Ser Phe Thr Ile Met Glu Ser Val Gly Asp His Pro His Ser Ala
            100                 105                 110

His Lys Tyr Tyr Cys Phe Ala Pro Ser Asp Asp Tyr Glu Asp Leu Gln
        115                 120                 125

Leu Pro Pro Ile Val Glu Glu Ser Asp Arg Lys Leu Phe Gln Val Leu
    130                 135                 140

Ala Val Gln Val Thr Leu Phe Pro Gly Arg Gly Val Cys Ile Gly Ile
145                 150                 155                 160

Thr Thr His His Thr Val Ser Asp Ala Pro Ser Phe Val Gly Phe Met
                165                 170                 175

Lys Ser Trp Ala Ser Ile Thr Lys Phe Gly Gly Asp Asp Glu Phe Leu
            180                 185                 190

Asp Gly Lys Gly Glu Cys Leu Pro Val Phe Asp Arg Ser Leu Val Asn
        195                 200                 205

Tyr Pro Pro Lys Leu Asp Thr Tyr Leu Trp Asn Asn Ala Gln Lys Arg
    210                 215                 220

Pro Leu Glu Ser Gln His Pro Ser Leu Pro Thr Asp Arg Ile Arg Ala
225                 230                 235                 240

Thr Tyr Leu Phe Thr Gln Ser Glu Ile Lys Lys Leu Lys Gly Leu Ile
                245                 250                 255

Gln Arg Lys Ala Pro Asn Val Val Asn Leu Ser Ser Phe Val Ala Ile
            260                 265                 270

Ala Ala Tyr Ile Trp Thr Gly Ile Ala Lys Ser Val Gly Asp Tyr Lys
        275                 280                 285

Asp Val Asp Asp Asp Lys Arg Ala Phe Phe Leu Ile Pro Ile Asp Leu
    290                 295                 300

Arg Pro Arg Leu Asp Pro Pro Ala Pro Gly Asn Tyr Phe Gly Asn Cys
305                 310                 315                 320

Leu Ser Phe Ala Met Ala Lys Ile Leu Arg Arg Asp Leu Val Gly Asp
                325                 330                 335

Glu Gly Val Phe Arg Ala Ala Glu Ala Ile Ala Glu Ile Glu Lys
            340                 345                 350

Arg Thr Ser Asp Lys Lys Ile Leu Glu Thr Val Glu Asn Trp Pro Ser
        355                 360                 365

```
                                              -continued

Glu Ile Arg Glu Ala Leu Gln Asn Cys Tyr Phe Ser Val Ala Gly Ser
        370                 375                 380

Ser Arg Leu Asp Leu Tyr Gly Ala Asp Phe Gly Trp Gly Lys Ala Val
385                 390                 395                 400

Lys Gln Glu Ile Leu Ser Ile Asp Gly Glu Lys Phe Thr Met Ser Leu
                405                 410                 415

Cys Lys Pro Arg Asp Ala Ala Gly Gly Leu Glu Val Gly Leu Ser Leu
            420                 425                 430

Pro Lys Glu Glu Leu Gln Ala Phe Asp Asp Tyr Phe Ala Glu Gly Ile
        435                 440                 445

Lys Gly
    450

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Glu Gln Ile Gln Met Val Ala Val Ile Glu Thr Cys Arg
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Glu Gln Ile Gln Met Val Asn Ile Leu Glu
 1               5                  10

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Thr Leu Leu Glu Ser
 1               5
```

US 7,105,719 B1

GENE ENCODING A PROTEIN HAVING ACYL GROUP TRANSFER ACTIVITY

FIELD OF THE INVENTION

The present invention relates to genes encoding proteins having aromatic acyl group transfer activity and the use thereof. More particularly, the present invention relates to genes encoding proteins having aromatic acyl group transfer activity derived from gentians (*Gentiana triflora* var. *japonica*), petunias (*Petunia hybrida*), perillas (*Perilla ocimoides*), and cinerarias (*Senecio cruertus*), and the use thereof.

BACKGROUND ART

The flower industry is making efforts to develop new and various varieties. An effective method of producing a new variety involves changing the color of a flower, for which the traditional breeding methods have been successfully employed to produce a wide variety of colors for almost all commercial varieties. With the above methods, however, it is rare that a single species produces colored varieties coming in a wide range of different colors since a pool of genes is limited for each species.

The colors of flowers are based mainly on two types of pigments, flavonoids and carotenoids. Flavonoids contribute mainly to the colors in the range of yellow to red and blue, while carotenoids contribute to the color tones of orange or yellow. Flavonoid molecules that make a major contribution to the color of flowers are anthocyans which are glycosides of cyanidin, delphinidin, petunidin, peonidin, malvidin, and pelargonidin. Different anthocyans impart-marked changes in the color of flowers. Furthermore, the color of flowers is affected by copigmentation with colorless flavonoids, metal complex formation, glycosylation, acylation, methylation and pH of vacuoles (Forkman, Plant Breeding 106: 1, 1991).

There are a number of reports of acylated anthocyans isolated from nature including cinerarin derived from cinerarias (*Senecio cruentus*) (Goto et al., Tetrahedron 25: 6021, 1984), awobanin derived from dayflowers (*Commelina communis*) (Goto and Kondo, Angew. Chem. Int. Ed. Engl. 30: 17, 1991) and gentiodelphin derived from *Gentiana Makinoi* (Yoshida et al., etrahedron 48: 4313, 1992) (*Monarda didyma*: Kondo et al., Tetrahedron 26: 5879, 1985; perillas, pansies (Goto et al., Tetrahedron 27:2413, 1987; Wandering Jew: Idaka et al., Tetrahedron 28: 1901, 1987; *Dioscorea japonica*: Shoyama et al., Phytochemistry 29: 2999, 1990; red cabbage, *Platycodon qrandiflorum, lobelia*, delphiniums, butterfly peas: Goto and Kondo, Angew. Chem. Int. Ed. Engl. 30:17, 1991; carrots: Glabgen et al., Phytochemistry 31: 1593, 1992; morning glory: Lu et al., Phytochemistry 32: 659, 1992; Saito et al., Phytochemistry 40: 1283, 1995; *Ajuga decumbens, Clinopodium gracile, Lamiums*, lavender, catnip, *Leonurus macranthus, Plectranthus, Prunellas, Salvias splendens* Sella, Janapnese Artichoke: Saito and Harborne, Phytochemistry 31: 3009, 1992; giant water lily: Strack et al., Phytochemistry 31: 989, 1992; bellflowers: Brandt et al., 33: 209, 1993; gentians: Hosokawa et al., Phytochemistry 40: 941, 1995; hyacinth: Hosokawa et al., Phytochemistry 40: 567, 1995).

Acyl groups which modify these anthocyan-containing flavonoids are divided into two classes based on their structure: one is the aromatic acyl groups centering on hydroxy cinnamic acids, and the other is the aliphatic acyl groups such as the malonyl group. It has been observed in the experiment carried out using the anthocyanin pigment of morning glories (*Pharbitis nil*) that among the acyl groups transfer reactions anthocyans to which an aromatic acyl group, preferably coumaric acid or caffeic acid, is bound show a shift of the absorption maximum to the long wavelength side (Dangle et al., Phytochemistry 34: 1119, 1993).

Furthermore, for cinerarin derived from cineraria (*Senecio cruentus*) which has one aliphatic acyl group and three aromatic acyl groups, it has been reported that the stability of the pigment decreases in a neutral aqueous solution by removing aromatic acyl groups (Goto et al., Tetrahedron 25: 6021, 1984). For gentiodelphin derived from gentians (*Gentiana makinoi*) also, it has been reported that an intramolecular stacking of the sandwich type occurs due to the presence of two aromatic acyl groups in the molecule, which results in stabilization of the pigment in an aqueous solution (Yoshida et al., Tetrahedron 48: 4313, 1992). Moreover, Yoshida et al. have demonstrated that each of glucose at position 5 and glucose at position 3' of anthocyanin has an acyl group bound thereto (Tetrahedron 48: 4313, 1992). It has also been reported that anthocyanin in the leaves of perillas (*Perilla ocimoides*) is shisonin in which coumaric acid is bound to glucose at position 3 of cyanidin 3,5-diglucoside (Tetrahedron Letters 27: 2413–2416, 1978).

However, these studies have been carried out from the aspect of organic chemistry such as structural studies of natural pigments and not from the aspect of biochemistry such as efforts to isolate enzymes which transfer acyl groups.

Of the transferases which transfer acyl groups to anthocyanin pigments, there are many reports on the malonyl group transferases which transfer an aliphatic acyl, including those from a cell culture of parsley (Matern et al., Arch. Biochem. Biophys. 208: 233, 1981; Matern et al., Arch. Biochem. Biophys. 226: 206, 1983; Matern et al., Eur. J. Biochem. 133: 439, 1983), seedlings of *Cicer arientium* (Koster et al., Arch. Biochem. Biophys. 234: 513, 1984), and the like.

Aromatic acyl transfer reaction was first reported for Silene, a member of Caryophyllaceae (Kamsteeg et al., Biochem. Physiol. Pflanzen 175: 403, 1980), and the activity of aromatic acyltransferase has similarly been found in the soluble enzyme fraction of Matthiola (Teusch et al., Phytochemistry 26: 991, 1986).

However, these reports have been limited to a mere demonstration of the presence of enzymatic activity, and neither the corresponding enzyme proteins have been specified nor findings have been obtained on the primary structure of the enzymes much less the genes encoding them. For other aromatic acyl transferases as well no reports have elucidated the primary structure of proteins or genes. Furthermore, there are no reports of examples in which the acylating reactions of anthocyanin pigments were positively used to expand the range of colors of flowers and to grow them, or examples in which acylation was used in an attempt to stabilize anthocyanins.

On the other hand, the biochemical pathway of synthesis of anthocyanins of *Petunia hybrida* has been well studied (Wiering, H. and de Vlaming, P. Inheritance and biochemistry of pigments. Petunia, P49–65 (1984), Griesbach, R. J., asen, S. and Leonhardt, B. A., Phytochemistry, 30: 1729–1731, 1991), and the presence of anthocyanins which contain an acyl group is known. As the acyl group of anthocyanins of Petunia, coumaric acid or caffeic acid is known. One molecule of coumaric acid or caffeic acid is bound to rutinoside at position 3 of anthocyanin, whose chemical structure, when the anthocyanidin is malvidin, has been assigned to 3-O-(6-O-(4-O-coumaroyl)-α-D-glucopyranosyl)-5-O-β-D-gluc opyranosyl-malvidin and 3-O-(6-O-(4-O-caffeoyl)-α-D-glucopyranosyl)-5-O-β-D-gluco pyranosyl-malvidin, respectively. However, there were no reports on anthocyanins having two acyl groups.

DISCLOSURE OF THE INVENTION

The present invention relates to genes encoding proteins having aromatic acyl group transfer activity and the use thereof. Thus, with regard to said use, there is described a method for controlling an acyl group transfer reaction to flavonoids, preferably anthocyanins, which provides a possibility of developing a wide range of flower colors for a single species. In particular, said method is considered to be useful for imparting bluish tints to the existing color of flowers, because the absorption maximum of anthocyanin shifts to the long wavelength direction by transfer of aromatic acyl groups.

In order to realize the above technology, it is necessary to elucidate the identity of enzymes responsible for aromatic acyl transfer reactions and to separate the cDNA which encodes said enzymes. Furthermore, by utilizing the homology of genes it is possible to separate the genes of other acyl group transfer enzymes. Moreover, production of stable anthocyanin pigments can be realized by acylation since acylation leads to increased stability of anthocyanins.

The inventors have isolated an acyltransferase from petals of gentians and determined the primary structure thereof. Furthermore, using recombinant technology we have also isolated cDNA's of acyltransferases of gentians, petunia, perillas, and cinerarias, and determined the nucleotide sequences of the structural genes. Thus, the present invention provides DNA sequences encoding acyltransferases which are present in the petals of gentians, petunias, and cineraria, and leaves of perillas. Furthermore, the enzymes of the present invention can be used to change the colors of flowers by acylating the anthocyanin pigments and to increase stability of anthocyanins.

Specific Description

Genes encoding acyltransferases may be obtained, for example, as follows. Thus, first an acyltransferase is purified from petals of gentians. Prior to the present invention all attempts to purify aromatic acyltransferases have failed. The inventors of the present invention have succeeded in purifying said enzyme for the first time by employing various chromatographic methods, especially affinity chromatography using a resin (for example, Blue Sepharose (TM) resin, etc.) on which is immobilized, for example, Cibacron Blue 3GA.

Then, the partial amino acid sequence of the acyltransferase is elucidated using the conventional method and a synthetic nucleotide corresponding said amino acid sequence is prepared.

On the other hand, poly A+RNA is extracted from petals of the same gentian, from which double stranded cDNA is synthesized using the conventional method and a cDNA library is further produced. Using the above double stranded cDNA as the template a DNA fragment specific to the gene of acyltransferase is obtained by the PCR method using the synthetic DNA primers which were used for synthesis of said synthetic DNA and cDNA. Then, using this DNA fragment as a probe, the above mentioned cDNA library is screened to obtain positive clones. Plasmid DNA which is recovered from the clones are separated and their nucleotide sequences are determined. Then the amino acid sequence obtained from analysis of the purified acyltransferase and the amino acid sequence of the acyltransferase deduced from the DNA nucleotide sequence are compared to confirm that the above positive clone is the desired cDNA clone.

The inventors have also found petunia mutant (VM) a mutant strain of petunia var. *Surfinia* purple (VM) (Suntory Ltd.), in which the color of the flower has been changed from red purple to purple, and determined the structure of anthocyanins according to the method as described by, for example, Yoshida et al. (Yoshida et al., Tetrahedron 48: 4313, 1992).

As the DNA of the present invention there is mentioned DNA encoding the amino acid sequence as set forth in any of SEQ ID No. 32 to 37 respectively. However, it is known that proteins having modified amino acid sequences in which several amino acids have been added, removed and/or replaced with other amino acids have enzymatic activity similar to the original protein. Accordingly, genes encoding proteins which have modified amino acid sequences wherein one or more amino acids have been added, removed and/or replaced with other amino acids are encompassed in the present invention.

The present invention also relates to genes encoding proteins which hybridize with the nucleotide sequence as set forth in any of SEQ ID No. 1 to 6 or a portion thereof, for example the portion encoding six or more amino acids of the consensus region, under the condition of, for example 2 to 5×SSC and 50° C., and which have acyl group transfer activity. Furthermore, the optimum hybridization temperature depends on the nucleotide sequence and its length. Preferably the hybridization temperature becomes low, as the nucleotide sequence becomes short. For example, in the case of the nucleotide sequence (18 bases) encoding six amino acids, a temperature of 50° C. or lower is preferred. The present invention also relates to genes encoding proteins having the amino acid sequence which has a homology of 15% or higher, preferably 25% or higher, for example 30% or higher with the amino acid sequence as set forth in any of SEQ ID No. 1 to 6, and which has aromatic acyl group transfer activity.

The DNA which has the original nucleotide sequence is obtained. as specifically described in Examples, by screening, for example a cDNA library.

DNA encoding the enzyme having a modified amino acid sequence can be synthesized by the conventional site-directed mutagenesis or a PCR method based on the DNA having the original nucleotide sequence. For example, a DNA fragment having a site which is desired to be modified is obtained by digestion with restriction enzymes of cDNA or genomic DNA obtained as above, which is then used as the template to obtain the DNA fragment having the desired modification inserted therein by site-directed mutagenesis or a PCR method, and by ligating this to the DNA which encodes other parts of the desired enzyme.

Alternatively, in order to obtain DNA encoding an enzyme having a shortened amino acid sequence, DNA encoding an amino acid sequence longer than the desired amino acid sequence, for example DNA encoding the full-length amino acid sequence is cut with the desired restriction enzyme. When the resulting DNA fragment does not encode the desired entire amino acid sequence, the missing portion can be complemented by ligating synthetic DNA.

A gene encoding acyltransferase according to the present invention can be obtained by expressing the above clone in *Escherichia coli* and yeast using gene expression systems, confirming that the gene obtained encodes acyltransferase, and elucidating the translation region of the gene of acyltransferase. Furthermore, by expressing said gene a genetic product, the protein of the desired acyltransferase can be obtained.

Alternatively, it is also possible to obtain said protein using an antibody against the amino acid sequence describe in any of SEQ ID No. 32 to 37 respectively.

Thus, the present invention relates to a recombinant vector comprising said DNA, in particular an expression vector, and a host transformed with said vector. As the host, a eukaryotic or prokaryotic organism may be employed. The prokaryotic organisms which may be used include a bacterium belonging to the genus *Escherichia*, for example, *Escherichia coli* a bacterium belonging to the genus *Bacillus*, for example *Bacillus subtilis*, or any other conventional hosts.

The eukaryotic organisms which may be used include lower eukaryotes, for example eukaryotic microorganisms, for example fungi such as yeast or filamentous fungi. As the yeast, there are mentioned *Saccharomyces* such as *Saccharomyces cereviciae*. and as the filamentous microorganisms, there are mentioned *Aspergillus* such as *Aspergillus oryzae* and *Aspergillus niger*, and *Penicillium*, and the like. Moreover, animal cells or plant cells may be used. The animal cells which may be used include cell lines of mouse, hamster, monkey, human, and the like. Furthermore, insect cells such as silkworm cells or larvae of silkworm themselves may be used as a host.

The expression vectors of the present invention contain expression regulating regions, for example promoter and terminater, replication origin, and the like depending on the kind of the host to which they are introduced. As a promoter for bacterial expression vectors, conventionally used promoters such as trc promoter, tac promoter, lac promoter, etc. may be used. As a promoter for yeast, for example, glyceraldehyde-3-phosphate dehydrogenase promoter, PH05 promoter, and the like may be used. As s promoter for filamentous organisms, for example, amylase, trp C, and the like may be used. As a promoter for animal cell hosts, viral promoters such as SV40 early promoter, SV40 late promoter, and the like may be used.

The construction of an expression vector may be carried out according to a conventional method using restriction enzymes, ligase, and the like. Transformation of hosts with an expression vector may also be carried out according to a conventional method.

In the manufacture of said proteins, the desired protein can be obtained by culturing, growing, or breeding a host transformed with the above-mentioned expression vector, and then subjecting the culture to gel-filtration, centrifugation, cell disruption, gel-filtration chromatography,-ion exchange chromatography, and the like to recover and/or purify said protein.

Although the invention has been described with specific reference to acyltransferases derived from gentians, petunias, perillas, and cinerarias, it should be noted that the purification method of said enzyme may be wholly or partially modified to purify acyltransferases of other plants and then the amino acid sequences of said enzymes are determined in order to clone genes encoding said enzymes. By using as a probe cDNA of acyltransferase derived from a gentian according to the present invention, it was also possible to obtain cDNA of another acyltransferase from a gentian and cDNA of another acyltransferase from a petunia. Accordingly, by using part or all of the gene of acyltransferase it is possible to obtain the gene of another acyltransferase. Comparison of these amino acid sequences revealed the presence of a region of a conserved amino acid sequence. By using this region it was also possible to obtain cDNA of acyltransferase of a *perilla* and a cineraria. A similar method can be applied to other plants to obtain cDNA or chromosomal DNA clone of a similar acyltransferase.

As has been described hereinabove, by purifying acyltransferases derived from a gentian, a petunia, a *perilla* and a cineraria and then obtaining antibody against said enzyme according to a conventional method, it is possible to clone cDNA or chromosomal DNA which produces a protein capable of reacting with said antibody. Thus, the present invention is not limited to acyltransferases derived from gentians, petunias, perillas and cinerarias, but relates broadly to aromatic acyltransferases.

Furthermore, the present invention relates to plants of which colors have been controlled by introducing gene of acyltransferase thereinto, or progenies thereof or their tissues, and they may be in the form of cut flowers.

Furthermore, in the present specification, CoA esters such as p-coumaroyl-CoA or caffeoyl-CoA etc. were mentioned as a donor of an acyl group in the acyl group transfer reaction of flavonoids involving anthocyanins, further more p-coumaroyl, ferulloyl, or hydroxycinnamoyl-1-O-glucose such as sinapoyl-1-O-glucose can also be used as a donor of an aromatic acyl group (Glassegen and Seitz, Planta 186: 582, 1992), and therefore enzymes according to the present invention can be used.

EXAMPLES

The present invention is now explained with reference to the following specific embodiments. The experimental procedures used were according to Molecular Cloning by Sambrook (Cold Spring Harbor Laboratory Press, 1989), unless otherwise specified.

Example 1

Search of Acyltransferase from Plants (1) Preparation of Substrate

Delphinidin 3,5-diglucoside and cyanidin 3,5-diglucoside were obtained from petals of Tapian violet (Suntory Ltd.), a breed of *Verbena hybrida*, by extracting a diacetylated form of each of the above and then by deacetylating them. Petals (348 g) of Tapian violet were homogenized with liquid nitrogen in a homogenizer, immersed in 1.5 L of 50% (v/v) acetonitrile and 0.2% trifluoro acetic acid (TFA), and then allowed to stand for three days.

The product thus obtained was filtered under aspiration through diatomaceous earth (#100) spread over filter paper then concentrated to half the volume in a rotary evaporator, followed by gel-filtration with HP-20 (Pharmacia). After washing with 800 ml of distilled water, the pigment fraction was eluted with 800 ml of 50% acetonitrile and 0.1% TFA. After concentration in an evaporator, it was lyophilized to obtain crude pigment (7.3 g).

Since the main pigments in Tapian are 3,5-diacetylglucoside of delphinidin and cyanidin, the following procedure of deacetylation was carried out. One gram of the crude pigment was dissolved in 50 ml of methanol and aerated with nitrogen gas for 15 minutes to expel dissolved oxygen and then cooled on ice.

Separately, dissolved oxygen was similarly expelled from 50 ml of 1 N sodium hydroxide, into which the above pigment solution was added dropwise while stirring in the ice, and was stirred for further 30 minutes to effect hydrolysis. One ml of 6 N hydrochloric acid was added thereto to stop the reaction. Then, 5 ml of distilled water was added and concentrated to half the volume in an evaporator, to which methanol was added to a final concentration of 10%. Two ml aliquots were applied to Sep Pac C18 column (Waters Association), which was then washed with 5 ml of distilled water, and eluted with 2 ml of 30% acetonitrile and 0.6% TFA.

All eluates were collected and concentrated in an evaporator, and then fractionated by HPLC. Using a DEVELOSIL ODS-10/20 (50×300 mm; Nomura Kagaku K.K.) column, elution was effected at a linear gradient of TFA from 0.1% to 0.3% and acetonitrile from 10% to 30% over 120 minutes. Fractions were collected every 0.5 minute at a flow rate of 32 ml per minute. Absorption spectrum of each pigment faction was measured to separate delphinidin-3,5-diglucoside and cyanidin 3,5-diglucoside, which were then concentrated and lyophilized (delphinidin-3,5-diglucoside, 75 mg and cyanidin 3,5-diglucoside, 50 mg). They were each dissolved in 0.5% TFA to a concentration of 1.5 mg/ml and stored at −80° C. until use.

Synthesis of another substrate, hydroxy cinnamoyl-CoA was carried out in the following manner. First, an ester was synthesized from caffeic acid (Nakalai tesque) and N-hydroxysuccinimide (Merck) according to a literature (Stockigt and Zenk, Z. Naturforsch. 30: 352, 1975). This ester (0.5 mmol) was dissolved in 2 ml of acetone. Separately 0.1 mmol of Coenzyme A (CoA: KOHJIN) and 1 mmol of sodium hydrogen carbonate were dissolved in 20 ml of water, to which was added dropwise the ester solution prepared above.

After the mixture was reacted overnight while stirring under nitrogen gas at room temperature, it was concentrated in a rotary evaporator and centrifuged (27,000×g, 10 min) to remove insoluble matter and the desired product was collected using HPLC. Using a DEVELOSIL ODS-10/20 (50× 300 mm; Nomura Kagaku K.K.) column, elution was carried out at a linear gradient of acetonitrile from 18% to 36% in the presence of 0.1% of TFA over 40 minutes. Fractions were collected every 0.8 minute at a flow rate of 32 ml per minute. The absorption spectrum of each fraction was measured (200 to 400 nm) to collect the fractions having an absorption maximum in the range of 344 to 348 nm as the caffeoyl CoA fraction. After concentration in a rotary evaporator, they were separated using the same column again.

However, elution was carried out by isocratic chromatography of 18% acetonitrile and 0.1% TFA, and the absorption spectrum was measured simultaneously to concentrate the fractions containing the desired compounds in a rotary evaporator, which were then lyophilized. This method produced 35 μmol of the products. By substituting coumaric acid for caffeic acid above, p-coumaroyl-CoA was synthesized. The product was dissolved in distilled water at 2 mg/ml and stored at −80° C. until use.

(2) Extraction Method of the Crude Enzyme Solution

Three grams of the plant tissue (petals, edible parts, etc.) from which enzyme was to be extracted was frozen in liquid nitrogen and was homogenized in a mortar. It was further homogenized by adding 10 ml of the extraction buffer (100 mM phosphate buffer, pH 7.5, 10 mM-sodium ascorbate, 14 mM 2-mercaptoethanol) and was filtered through three layers of gauze. After adding 3 g of DOWEX (1-X2, 100–200 mesh; Muromachi Kagaku Kogyo K.K.) and stirred for 10 minutes, the resin was removed by filtration under aspiration and the debris of the plant tissue was removed by centrifugation (27,000×g, 20 minutes). It was then subjected to salting out under 70% saturated ammonium sulfate to precipitate proteins. The precipitate was suspended into 1 ml of the solubilizing buffer (20 mM phosphate buffer, pH 7.5, 14 mM 2-mercaptoethanol) and insoluble matter was removed by centrifugation (27,000×g, 5 minutes). Then it was desalted using Sephadex G-25 column (NAP-10; Pharmacia) which had been equilibrated with the solubilizing buffer and the solution thus obtained was used as the crude enzyme solution.

(3) Method of Measuring Enzyme Activity

Fifty μl of a reaction mixture containing 100 mM phosphate buffer, pH 8.5, 24 nmol of delphinidin 3,5-diglucoside, 21.5 nmol of caffeoyl-CoA, and 20 μl of the enzyme solution was reacted at 30° C. for 10 minutes. After stopping the reaction by adding 50 μl of acetonitrile containing 13.8% (v/v) acetic acid and insoluble matter was removed by centrifugation (18,000×g, 5 minutes), it was analyzed by high performance liquid chromatography (HPLC). Twenty μl of the reaction mixture was analyzed using a C18 reverse phase column (YMC-Pack ODS-A, 6.0×150 mm; YMC) and 21.6% acetonitrile and 0.1% trifluoroacetic acid at a flow rate of 1 ml per minute. The compounds were detected using a three dimensional chromatography system (CLASS-LC10; Shimazu Seisakusho, K.K.) and it was found that the product has an absorption maximum at about 330 nm which is absent in the substrate and that the absorption maximum in the visible light range shifted by about 6 nm from 519 nm to 525 nm, confirming that an acyl group (caffeic acid) is bound, and delphinidin 3-glucosyl 5-caffeoyl glucoside has been produced.

By detecting at a wavelength of 520 nm, the ratio of the peak area of the product (delphinidin 3-glucosyl 5-caffeoyl glucoside) to the sum of the peak areas of the substrate (delphinidin 3,5-diglucoside) and the product (delphinidin 3-glucosyl 5-caffeoyl glucoside) was determined to calculate the mole number of the product, which was defined as the enzymatic activity (kat). The retention time for each compound in this HPLC analysis was as follows: caffeoyl-CoA, 6.3 min; delphinidin 3,5-diglucoside, 3.3 min; delphinidin 3-glucosyl 5-caffeoylglucoside, 5.3 min.

Since under this reaction condition delphinidin 3,5-diglucoside in the reaction mixture is modified with caffeic acid by the action of acyltransferase resulting in color change of the reaction mixture from dark blue to reddish purple, the enzymatic activity can be determined, as a simple method, by carrying out the reaction in a microtiter plate.

When the plate after the reaction is allowed to stand at room temperature for a prolonged period of time (one day to one week), delphinidin 3,5-diglucoside which was not acylated becomes colorless, whereas the delphinidin 3,5-diglucoside which was acylated by the action of the enzyme retains the reddish purple color, so that stabilization of delphinidin 3,5-diglucoside in a neutral to alkaline solution was observed because of its acylation. Similarly, when cyanidine 3,5-diglucoside was used as the substrate, the color of the reaction mixture changed from reddish purple to dark blue and the pigment becomes stabilized, and hence it is possible to detect the enzymatic activity by a simple enzyme assay.

On the other hand, when caffeoyl-CoA is replaced with p-coumaroyl-CoA, acylation-derived color change and stabilization of anthocyanin are observed, but the degree of change in the tone of color is smaller than with caffeoyl-CoA.

(4) Search for Acyltransferase

Crude enzyme solutions were extracted from a variety of plants including gentians, iris, delphiniums, stocks, *Eustoma russellianum Griseb*, pinks, sweet peas, Larkspurs, pansy, cinerarias (petals for the above plants), red cabbages, red onions, Kintoki carrots, western carrots, purple potatoes, perillas (edible parts for the above plants) and egg plants (epithelial part of the fruit), and their enzymatic activities were determined. As a result, acyltransferase activities of 0.63, 0.0012, and 21.8 nkat/mg protein were detected in the extracts from *Eustoma russellianum Griseb*, pinks, and gentians, respectively. Gentian, which had the highest acyltransferase activity per protein extracted, was used as a material for enzyme purification.

Determination of protein concentration was carried out using the Bio-Rad Protein Assay (Bio-Rad).

Example 2

Purification of Acyltransferase Derived from Gentians (1) Purification of Enzyme Enzyme was extracted from petals of *Gentiana triflora* var. *japonica*. The following experiment was carried out at 0 to 4° C. unless otherwise noted. Three kilograms of petals of Gentiana triflora var. *japonica* was homogenized in the presence of liquid nitrogen using the Excell Auto Homogenizer (DX-3; Nihoh Seiki Seisakusho). After adding 8 L of the extraction buffer (100 mM phosphate buffer, pH 7.0, 10 mM sodium ascorbate, 10 µM p-amidinophenyl methanesulfonyl fluoride hydrochloride (p-APMSF; Wako Pure Chemicals K.K.)), 5 mM dithiothreitol (DTT; Nakalaitesk), and 500 g of polyclar SB-100 (Wako Pure Chemicals K.K.), it was completely pulverized.

After the pulverized liquid was squeezed with 4 layers of gauze, it was further centrifuged (11,000×g, 30 min) to remove cell debris. Then it was salted out with 40% saturated ammonium sulfate and insoluble matter was removed prior to salting out again with 70% saturated ammonium sulfate. The precipitate was suspended into 250 ml of the solubilizing buffer (20 mM Tris-HCl, pH 7.0, 10 µM p-APMSF, 1 mM DTT), and insoluble matter was removed by centrifugation. Then it was desalted using Sephadex G-25 column (95×110 mm; Pharmacia) which had been equilibrated with the same buffer. The protein-containing fractions were collected (860 ml) and subjected to the following chromatography.

Each of chromatographies of Q-Sepharose Fast Flow, HiTrap Blue and Phenyl Superose were carried out using the FPLC system (Pharmacia).

First, the samples were applied to Q-Sepharose Fast Flow (26×100 mm; Pharmacia) which had been equilibrated with the same buffer. After adequately washing the column with the same buffer, it was eluted with a liner gradient of sodium chloride from 0 M to 0.4 M in 60 minutes (8 ml/min). After the fractions containing enzymatic activity were pooled (130 ml), they were subjected to affinity chromatography. It was then applied to three columns of HiTrap Blue (5 ml, 16×25 mm; Pharmacia) connected in a series, adequately washed with the same buffer, and eluted with the same buffer containing 1 M sodium chloride. The active fractions were salted out with 70% saturated ammonium sulfate to obtain a protein precipitate.

The precipitate was suspended in 1 ml of the solubilizing buffer and insoluble matter was removed by centrifugation, and then was applied to Sephacryl S-200 (25×1150 mm; Pharmacia) which had been equilibrated with the solubilizing buffer. At a flow rate of 0.2 ml per minute about 3 ml fractions were collected and after the active fractions were collected again (27 ml), sodium ammonium was added thereinto to a concentration of 1 M. After fully stirring, it was centrifuged (39,000×g, 10 min) to remove insoluble matter and applied to Phenyl Superose 5/5 (5.0×50 mm; Pharmacia) which had been equilibrated with the solubilizing buffer-containing 1 M sodium ammonium.

After adequately washing at a flow rate of 0.5 ml, the concentration of sodium ammonium was linearly decreased from 1 M to 0 M over 60 minutes to elute protein. A 0.5 ml aliquot of each fraction was measured for enzymatic activity. In an analysis by SDS-polyacrylamide gel electrophoresis a band of molecular weight about 50,000 was observed as an almost single protein and since correlation was observed between this protein and activity, the protein was concluded to be the desired acyltransferase. The fractions (12 ml) having activity were further purified by reverse phase HPLC in order to obtain a single product.

Using a DEVELOSIL 300 C4-HG-5 (4.6×250 mm; Nomura Kagaku K.K.) column, elution was carried out at a linear gradient of acetonitrile from 40.5% to 56.7% in the presence of 0.1% trifluoroacetic acid over 30 minutes at a flow rate of 1 ml per minute. One ml fractions were collected while monitoring absorbance at 280 nm. Each fraction was further analyzed by SDS-polyacrylamide gel electrophoresis to collect fractions containing protein of molecular weight about 50,000. By repeating this HPLC for 30 times and concentrating in a speed Vac Concentrator (Savant), about 0.2 ml of single protein product was obtained.

(2) Analysis of Purified Protein

When 500 pmol of purified product was subjected to the amino acid sequencer (PSQ-1; Shimazu Seisakusho K.K.), 200 pmol of glutamic acid at the first stage of Edman degradation and 90 pmol of glutamic acid at the second stage were detected, but not at the third stage and thereafter. Accordingly, it was inferred that the N-terminal of the enzyme was blocked in some way or other.

However, since it is known that when the N-terminal is glutamic acid, pyroglutamic acid is formed and the sequence as described above-by-Edman-degradation is observed, it is highly probable that the N-terminal of the enzyme is glutamic acid.

The remainder of the precipitate was dissolved in a solution containing 80 µl of 45 mM Tris-HCl, pH 8.5, 3.6 M urea, and 0.09% SDS, to which was added 16 pmol of lysyl endopeptidase (Lysyl Endopeptidase: derived from *Achromobactor lyticus*; Wako Pure Chemicals K.K.) and was reacted at 37° C. for 6 hours. The reaction mixture was separated directly by a DEVELOSIL 300 C4-HG-5 column.

The separation condition was a flow rate of 0.7 ml of a linear gradient of acetonitrile from 0% to 80% over 70 minutes in the presence of 0.1% trifluoroacetic acid. By monitoring absorbance at 210 nm fragments having a peak absorbance were collected. Out of 13 peak fractions thus obtained, three fractions which eluted at acetonitrile concentrations of 32% to 40% were concentrated in the Speed Vac Concentrator and then separated and purified using an ODS column (DEVELOSIL 300 ODS-HG-5; Nomura Kagaku K.K.) under the same condition as above.

Each fraction was concentrated to dryness in the Speed Vac Concentrator, dissolved in 30 µl of 40% acetonitrile, and then subjected to the amino acid sequencer. As a result, the amino acid sequences of six peptides were able to be analyzed. The amino acid sequence for each peptide is shown below (the sequence is shown in the direction from the amino terminus to the carboxy terminus):

Amino acid sequence (AT73): Arg-Phe-Leu-Gly-Ile-Thr-Gly-Ser-Pro-Lys (SEQ ID No. 7)

Amino acid sequence (AT72): Ile-His-Met-Asp-Ala-Phe-Ala-Lys (SEQ ID No. 8)

Amino acid sequence (AT741-1): Gly-Val-Glu-Ile-Gly-Val-Ser-Leu-Pro-Lys (SEQ ID No. 9)

Amino acid sequence (AT741-2): Ala-Ser-Leu-Ser-Leu-Thr-Leu-Lys (SEQ ID No. 10)

Amino acid sequence (AT9): His-Tyr-Val-Pro-Leu-Ser-Gly-Asn-Leu-Leu-Met-Pro-Ile-Lys (SEQ ID No. 11)

Amino acid sequence (AT83): Val-Arg-Ala-Thr-Tyr-Val-Leu-Ser-Leu-Ala-Glu-Ile-Gln-Lys (SEQ ID No. 12)

Example 3 cDNA Cloning of Acyltransferase Derived from Gentians (1)

(1) Construction of cDNA Library

Petals were collected from commercial gentians (*Gentiana triflora* var. *japonica*) and homogenized under liquid nitrogen in a mortar. From the homogenate, RNA was obtained by the method utilizing guanidine thiocyanate/cecium chloride and then poly A+RNA was obtained using the Oligotex (Nihon Roche) in the method recommended by the manufacturer. The method using guanidine thiocyanate/cecium chloride was carried out according to the method described in detail in R. McGookin, Robert J. Slater et al., Methods in Molecular Biology vol. 2 (Human Press Inc. 1984).

Using the obtained poly A+RNA as the template, double stranded cDNA was synthesized using the ZAP-cDNA synthesis kit (manufactured by Stratagene) and was cloned into phage vector λZAPII. Furthermore, using the GigapackII Gold Packaging Extract kit of the same company cDNA library was constructed by the method described in the kit insert.

(2) Designing Synthetic DNA Primers

Among the amino acid sequences obtained in Example 2, the sequence represented by Ile-His-Met-Asp-Ala-Phe-Ala-Lys (SEQ ID No. 13) is very likely to be Lys-Ile-His-Met-Asp-Ala-Phe-Ala-Lys (SEQ ID No. 14) considering the specificity of lysyl endopeptidase. Using the portion represented by the amino acid sequence: Lys-Ile-His-Met-Asp-Ala-Phe-Ala (SEQ ID No. 15) in this sequence, the following oligonucleotide was synthesized:

Nucleotide sequence (Oligo 1): 5'-AARATHCAYATG-GAYGCITTYGC-3' (SEQ ID No. 16).

Here, the sequence of nucleic acids is shown by the one-letter code in accordance with IUPAC-IBU. That is, A: adenine, C: cytosine, G: guanine, T: thymine, Y: C or T, R: A or G, H: A or C or T, and I: inosine.

Furthermore, another oligonucleotide shown below was also synthesized based on the primer used for construction of the cDNA library mentioned above:

Nucleotide sequence (Oligo 2): 5'-CTC-GAGTTTTTTTTTTTTTTTT-3' (SEQ ID No. 17)

(3) Cloning of Fragments of the Acyltransferase Gene

Using about 0.1 μg of double stranded cDNA derived from RNA of petals of gentians and Oligo 1 and Olig 2 as primers, the PCR reaction was carried out. The reaction was carried out using the polymerase chain reaction kit Gene Amp (Takara Shuzo K.K.) for 35 cycles with one cycle comprising 95° C. for 1 minute, 45° C. for 1 minute, and 72° C. for 2 minutes. When the reaction product thus obtained was run on a 1% agarose gel electrophoresis, a specific DNA fragment of about 400 bp was observed. This DNA fragment was recovered and 10 ng thereof was subjected to 25 cycles of the above-mentioned polymerase chain reaction using the DIG-nucleotide mixture (Boehringer) and synthetic nucleotide I and II to obtain DIG-labelled DNA fragments.

(4) Cloning of cDNA of Acyltransferase

λ phage library obtained as above was infected to *E. coli* strain XL1-Blue (Stratagene) to screen five plates (diameter, 13.5 cm) containing 50,000 plaques per plate.

Phage was adsorbed to a filter (Hybond N+, Amersham) and treated in the method recommended by the manufacturer, and then the filter was allowed to remain in the hybridization buffer (5×SSC, 50% formamide, 50 mM sodium phosphate buffer, pH 7.0, 7% SDS, 2% Blocking reagent (Boehringer), 0.1% lauloyl sarcosine, 80 mg/ml salmon sperm DNA) at 42° C. for 1 hour. The DIG-labelled DNA fragment obtained above was added to the hybridization solution and incubated for 16 hours.

The filter was washed with a washing solution (0.2×SSC, 0.1% SDS) and then an enzymeimmunoassay (Boehriner Mannheim) using the DIG-specific antibody labelled with alkaline phosphatase was carried out to detect by color development using 5-bromo-4-chloro-3-indolyl phosphate and nitroblue tetrazolium salt. The detection method used was as set forth in the manufacturer's instructions.

As a result, a few dozen positive clones were obtained. From 20 clones of them cDNA was collected on the plasmid pBluescript SK–. Insertion of cDNA was examined by agarose gel electrophoresis and it was found that the insertion of cDNA's of varying sizes was observed in all clones and the longest among them was 1.7 kb. Among them 9 clones were chosen and were subjected to analysis by restriction enzymes. Accordingly, it was found that similar patterns of restriction enzyme cleavage were observed, though their sizes were varied.

(5) Determination of Nucleotide Sequence

Plasmid was extracted from the clones thus obtained. Using the AB1373A DNA Sequencer (Perkin Elmer), for six clones (pGAT2, pGAT3, pGAT4, pGAT7, pGAT8, and pGAT11) out of nine which are considered to contain the full-length, the nucleotide sequence of the 5' end of cDNA was determined by the dideoxy sequence method using the fluorogenic reagents recommended by the same manufacturer.

The result suggested that these clones have the same nucleotide sequence and differ in the length of cDNA. From among these clones, the entire nucleotide sequence of pGAT4 was determined. Determination of the nucleotide sequence was carried out for each clone after a series of deleted clones were obtained using the Deletion Kit for Kilo-Sequence (Takara Shuzo, K.K.).

(6) Comparison of the Nucleotide Sequence with the Amino Acid Sequence cDNA which was inserted into pGAT4 represented 1703 bases, which was found to contain an open reading frame (ORF) comprising 1410 bases (containing the stop codon). The sequence is shown in the sequence listing SEQ ID No. 1. Since all of the partial amino acid sequences of the acyltransferase revealed in Example 2 occurred as amino acid sequences in the ORF, it was concluded that the cloned cDNA was the gene of acyltransferase derived from gentians. Analysis of the amino terminal of the initiation codon suggested that glutamic acid is the residue of the amino terminal, so that it was inferred that the first ATG from the 5' end was the initiation codon on the nucleotide sequence of the cDNA.

On the other hand, since the cDNA of pGAT8 is shorter than pGAT4 by 7 bases at the 5' end, it was suggested that this was not the full-length cDNA.

Example 4

Expression of Genes in E. coli (1) Construction of Expression Plasmid pTrc99A (Pharmacia), an E. coli expression vector, was used for expression of the acyltransferase gene of E. coli. This pTrc99A contains E. coli trc promoter which can be induced by isopropyl-β-D-thiogalactopyranoside (IPTG) and therfore by inserting the desired gene downstream of said promoter the gene can be expressed in E. coli.

A restriction enzyme NcoI site has been inserted thereinto by making use of the initiation codon, ATG sequence, so that direct expression of the desired gene from the initiation codon is possible by recombining it with NcoI.

pGAT10 was constructed by recombining the 1.8 kb DNA fragment (containing all nucleotide sequences as set forth in SEQ ID No. 1) obtained by digestion of pGAT4 with EcoRI and KpnI which are present in the present vector with the EcoRI and KpnI sites of the above-mentioned pTrc99A.

In order to introduce a NcoI site in the vicinity of the initiation codon of the acyltransferase, the following two oligonucleotides were synthesized which correspond to the vicinity of the initiation codon and the inside of the acyltransferase (about 300 bases from the initiation codon):

Oligonucleotide (GAT-NcoI): 5'-TTCACCATGGAG-CAAATCCAAATGGT-3' (SEQ ID No. 18)

Oligonucleotide (GAT-ScaI): 5'-CGAGTCGCCCTCAT-CAC-3' (SEQ ID No. 19)

With 10 ng of pGAT4 as the template, a PCR reaction was carried out using the above oligonucleotides as the primers. The reaction was carried out using the polymerase chain reaction kit Gene Amp (Takara Shuzo K.K.) for 15 cycles with one cycle comprising 95° C. for 1 minute, 56° C. for 1 minute, and 72° C. for 2 minutes. When the reaction product thus obtained was run on a 1% agarose gel electrophoresis, a specific DNA fragment of about 300 bp was observed. This DNA fragment was collected and cleaved with restriction enzymes NcoI and AatI. It was then ligated to a 6 kg fragment which was obtained by cleaving pGAT101 with NcoI and AatI to construct pGAT102. It was confirmed that the nucleotide sequence of the PCR-amplified portion was the same as that of pGAT4 after construction of pGAT102.

(2) Expression of Acyltransferase Gene in E. coli pGAT102 was used to transform E. coli MM294 (supE44 hsdR endA1 pro thi) (Meselson and Yuan, Nature, 217: 1110-, 1968). The host used here need not be specifically defined and may be any E. coli host which can be used as the host for transformation, and other strains (such as JM109, DH5, etc.) which are generally used for transformation and which are readily available to those skilled in the art can be employed. The method for transforming E. coli was as described by Hanahan (J. Mol. Biol., 166: 557-, 1983). The transformed E. coli was inoculated into 2 ml of LB medium (trypton 10 g, yeast extract 5 g, sodium chloride 10 g were dissolved in one liter of distilled water and pH was adjusted to 7.2 with sodium hydroxide) and incubated at 37° C. overnight.

One ml of the culture liquid was inoculated into 10 ml of M9 medium (sodium hydrogen phosphate 0.6%, potassium dihydrogen phosphate 0.3%, sodium chloride 0.5%, ammonium chloride 0.1%, glucose 0.5%, magnesium sulfate 1 mM, vitamin B1 4 μg/ml, pH 7.2) to which were added 0.5% casamino acid and 50 μg/ml of ampicillin, and cultured at 37° C. for 3 hours, and then 40 μl of 0.5 M IPTG (the final concentration, 2 mM) was added and culture was continued for 5 more hours. After harvesting the cells, they were washed with 30 mM Tris-HCl buffer, pH 7.5, containing 30 mM sodium chloride, and then the washed cells were suspended into 1 ml of the same buffer. To the cells were added 1 mg of lysozyme, 25 μl of 0.25 M EDTA, and allowed to stand at 0° C. for 30 minutes. The cells were then frozen and thawed for three times to disrupt the cells.

After centrifugation at 15,000 rpm for 30 minutes, the supernatant obtained was used as a crude enzyme solution and the enzymatic activity thereof was determined in the method for determination of enzymatic activity as set forth in Example 1(3). In the microtiter plate method the acyl group transfer reaction was confirmed in E. coli to which pGAT102 was introduced. Accordingly, they were analyzed by HPLC.

As a result it was found that in the E. coli into which pGAT102 was introduced, 18.3 nmol of delphinidin 3-glucosyl 5-caffeoyl glucoside was formed from 24 nmol of delphinidin 3,5-diglucoside and 21.5 nmol of caffeoyl-CoA.

Combining this result with the known fact that in anthocyanin of gentian the acyl group is bound to glucose at position 5 and position 3', it was revealed that the acyltransferase encoded by pGAT4 catalyzes the reaction of transferring an acyl group to glucose at position 5 of anthocyanin 3,5-diglucoside.

Furthermore, delphinidin 3,5-diglucoside which was acylated by acyltransferase produced in E. coli have also shown a stable color development when allowed to stand at room temperature for a prolonged period of time similarly to the one acylated by acyltransferase obtained by purifying from gentian.

Example 5

Expression of Genes in Yeast (1) Expression Vector in Yeast

As the expression vector of yeast, pYE22m as described in Japanese Unexamined Patent Publication (Kokai) No. 4-228078 was used.

(2) Expression of the Acyltransferase Gene in Yeast

About 1.8 kb of DNA fragment obtained by digesting either pGAT4 or pGAT8 at restriction enzyme sites, EcoRI and KpnI, present in each of said vectors was ligated to about 8 kb of DNA fragment obtained by digesting similarly pYE22m at EcoRI and KpnI sites to construct yeast expression vectors PYGAT4 and pYGAT8. PYGAT4 starts translation at the first methionine, but pYGAT8 which lacks part of 5' end of the isolated cDNA starts translation not at the translation initiation methionine of acyltransferase (number of amino acid sequence in the sequence listing SEQ ID No.: 32), but at the next methionine (number of amino acid sequence in the sequence listing SEQ ID No.: 36).

In these yeast expression vectors, the cDNA encoding acyltransferase is ligated downstream of the promoter for glyceraldehyde-3 phosphate dehydrogenase, one of the constitutive yeast promoters, and its transcription has been regulated by said promoter.

Using the method by Ito et al. (Ito et al., J. Bacteriol., 153: 163–168, 1983), a yeast *Saccharomyces cereviciae* G1315 (Ashikari et al., Appl. Microbiol. Biotechnol. 30, 515–520, 1989) was transformed. The transformed yeast was selected based on its recovery of synthetic ability of tryptophan.

It should be noted that the yeast host as used herein for transformation is not limited, but it may be any strain which displays a tryptophan requirement due to its incomplete TRP1 gene (for example, one commercially available from the Yeast Genetic Stock Center; Berkely, Calif., USA; Catalogure 7th edition (1991), page 36).

The transformant obtained was cultured under shaking in 10 ml of Burkholder medium (Burkholder, Amer. J. Bot. 30: 206–210) containing 1% casamino acid. As a control experiment, the yeast which has spontaneously recovered its synthetic ability of tryptophan was cultured in a similar manner.

After havesting the cells, they were washed with the same amount of the cell disruption buffer (30 mM Tris-HCl, pH 7.5, 30 mM sodium chloride), and suspended further in 1 ml of the same buffer and then was transferred into a 1.5 ml Eppendorf tube. After centrifugation, the supernatant was removed and the precipitated cells were resuspended into 0.4 ml of the same buffer, to which was added 400 mg of glass beads (Glass Beads 425–600 microns Acid-Wash, Sigma) and shaken vigorously to disrupt the yeast cells.

The supernatant after centrifugation was used as a crude enzyme solution and the enzymatic activity thereof was determined by the method for determination of enzymatic activity as set forth in Example 1(3). Since acyl group transfer reaction was observed by the microtiter plate method in all yeasts into which pYGAT4 and pYGAT8 were introduced, they were then analyzed by HPLC. The yeast used as the control did not show any activity of acyl group transfer.

The result indicated that 16.6 nmol and 20.9 nmol of delphinidin 3-glucosyl 5-caffeoyl glucoside were formed from 24 nmol of delphinidin 3,5-diglucoside and 21.5 nmol of caffeoyl-CoA, respectively in the yeast into which pYGAT4 and pYGAT8 were introduced. Both of the proteins which were produced by pYGAT4 and pYGAT8 had acyl group transfer activity though their amino termini were different.

Furthermore, delphinidin 3,5-diglucoside which was acylated by the acyltransferase produced by the yeast have shown a stable coloration even when allowed to stand at room temperature for a prolonged period of time similarly to the one acylated by the acyltransferase obtained by purifying from gentians.

Example 6 cDNA Cloning of the Acyltransferase Derived from *Gentian* (2)

Among the DNA fragments obtained by digestion of pGAT4 as set forth in Example 3(6), i.e. pGAT4 having the DNA as set forth in the sequence listing SEQ ID No. 1, with restriction enzymes EcoRI and NdeI, two DNA fragments which contain the translation region of acyltransferase were collected together and labelled with DIG as in the methods mentioned above. Using this as a probe, the phage of cDNA library from petals of gentians was adsorbed onto a filter (Hybond N+, Amersham), which was then regenerated by removing the pigments and the DIG labels attached to the filter according to the method recommended by the manufacturer (Amersham) and subjected to hybridization in a low concentration formamide hybridization buffer (5×SSC, 30% formamide, 50 mM Tris-HCl, pH 7.5, 1% SDS) at 42° C. for 16 hours.

After washing at 50° C. in the wash solution (5×SSC, 0.1% SDS), the filter was allowed to develop color as described in Example 3(4). A few dozen clones developed color. Out of the clones which developed color, 12 clones which did not develop color in Example 3(4) were obtained. The nucleotide sequences of cDNA of these clones were determined from the 5' end in the above-mentioned method to find that the nucleotide sequences of 11 clones coincided with that of pGAT4, but one clone did not, which was designated as pGAT106.

The entire nucleotide sequence of pGAT106 was determined as described above. The cDNA introduced into pGAT106 represented 1622 bases in length, in which an ORF comprising 1440 bases (containing the stop codon) was found. This is shown in the sequence listing SEQ ID No. 2. For the ORF contained in SEQ ID No. 2, its homology was examined with the entire region of the amino acid sequence encoded by pGAT4. The homology was found to be 38%.

Since the amino acid sequence encoded by pGAT106 is homologous with that of the enzyme encoded by pGAT4, it is inferred that the former has a similar enzymatic activity, i.e. an activity of catalyzing acyl group transfer to anthocyanins. The fact that the anthocyanin of gentians has acyl groups at glucose molecules at position 5 and 3' suggests that pGAT106 catalyzes the enzymatic reaction of transferring an acyl group to position 3' of anthocyanin. The result indicates that acyltransferases may be different in the positions of sugars of anthocyanins which they transfer an acyl group but that the amino acid sequences and the nucleotide sequences encoding them are homologous.

As hereinabove described, there are many anthocyanins which have acyl groups, and these compounds vary widely in the number and position of acyl groups. Accordingly, it is expected that there are a number of enzymes which catalyze acyl group transfer reaction. It is readily inferred that the amino acid sequences of these enzymes have homology with the amino acid sequences of pGAT4 and pGAT106 obtained herein. Based on this other acyltransferase genes can be obtained.

Example 7

Anthocyanin of Petunias

Anthocyanins found in a mutant (VM) in which the color of the flower was changed to purple from the original reddish purple of *Petunia hygrida* ver. Surfina purple (Suntory Ltd.), a breed of, was extracted by pulverizing petals thereof in liquid nitrogen and then extracting with 50% acetonitrile and 0.1% TFA. After filtration, the filtrate was separated and purified by ODS and ODP reverse phase column chromatographies. When one of the compounds was analyzed in detail by FABMS, $^1$H NMR, and $^{13}$C NMR, a new anthocyanin was found. Its structure is shown below;

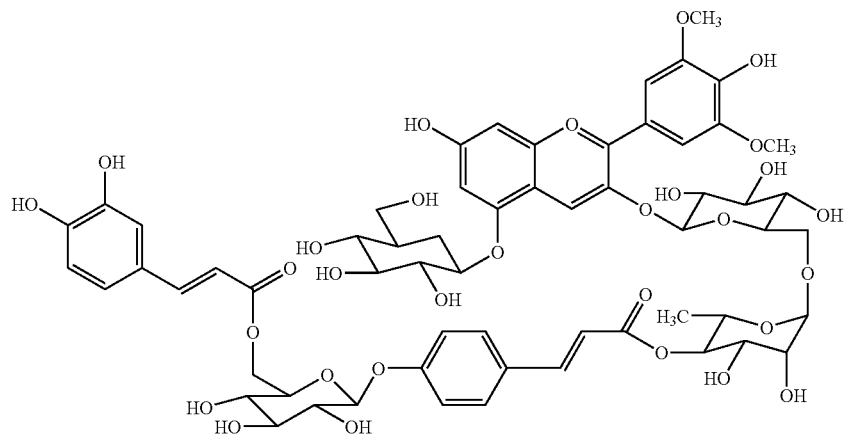

That is, the structure was 3-O-(6-O-(4-O-(4-O-(6-O-caffeoyl-β-D-glucopyranosyl)-coum aroyl)-α-L-ramnosyl)-β-D-glucopyranosyl)-5-O-β-D-glucopyr anosyl-malvidin, or an anthocyanin to which two acyl groups are bound.

In addition, 3-O-(6-O-(4-O-(4-O-(6-O-coumaroyl-β-D-glucopyranosyl)-cou maroyl)-α-L-ramnosyl)-β-D-glucopyranosyl)-5-O-β-D-glucopy ranosyl-malvidin, 3-O-(6-O-(4-O-(4-O-(6-O-caffeoyl-O-β-D-glucopyranosyl)-caff eoyl)-α-L-ramnosyl)-β-D-glucopyranosyl)-5-O-β-D-glucopyra nosyl-malvidin, 3-O-(6-O-(4-O-(4-O-(6-O-coumaroyl-β-D-glucopyranosyl)-caf feoyl)-α-L-ramnosyl)-β-D-glucopyranosyl)-5-O-β-D-glucopyr anosyl-malvidin were also detected. The anthocyanins were found to be present in the dark purple petals of Fulcon Blue (Sakata Seed Corp.), Old Glory Blue (Ball Seeds), and the like. Thus, anthocyanins having two acyl groups conceivably contribute to the dark purple color of petunias.

Accordingly, the foregoing suggests that acyltransferases related two arthocyanins derived from petunia come in two types: the enzyme which catalyzes a reaction of transferring coumaric acid or caffeic acid to rutinoside at position 3 of anthocyanin, and the enzyme which catalyzes a reaction of transferring coumaric acid or caffeic acid to monoacyl malvidin via glucose.

Example 8 cDNA Cloning of the Acyltransferase Derived from Petunias cDNA portion of pGAT4 described in Example 3(6), i.e. pGAT4 having DNA as set forth in the sequence listing SEQ ID No. 1, was labelled with DIG in the method described above, and the cDNA library of petals of Petunia hybrida var. Old Glory Blue was screened by the plaque hybridization technique. Hybridization and washing were carried out under the condition similar to the one as set forth in Example 6.

About 200,000 clones were screened, from which one weakly hybridizing clone was obtained. This clone was designated as pPAT5. Determination of the nucleotide sequence revealed that more than one DNA were inserted in pPAT5. Thus, there was a sequence similar to that of C-terminal of the protein encoded by pGAT4 and pGAT106 in the reverse primer side of the plasmid. Based on the reverse primer, a nucleotide sequence: 5'-AACAGCTAT-GACCATG-3' (SEQ ID No. 20) was synthesized and the oligonucleotide was designated as the RP primer.

In order to obtain the full-length cDNA of pPAT5, 100 ng each of the RP primer and the oligo 2 primer, and 10 ng of pPAT5 digested with XhoI were subjected to PCR reaction in a final volume of 50 μl. The reaction cas carried out for 20 cycles with one cycle comprising 95° C. for 1 minute, 55° C. for 1 minute, and 72° C. for 1 minute. The DNA fragment of about 600 bp thus obtained was run on an agarose gel electrophoresis and purified by GENECLEAN. After the fragment was enzyme digested with SmaI, the DNA fragment of about 400 bp was purified in a similar manner. The DNA fragment was labelled with the above-mentioned DIG.

Using the labelled DNA fragment, the above cDNA library of petals of petunias was screened by the plaque hybridization technique. Washing after hybridization was carried out in 0.2×SSC at 65° C. for 1 hour. Determination of the nucleotide sequence of the plasmid recovered from the clone obtained revealed that pPAT48 contained the same sequence as pPAT5 does. This is shown in the sequence listing SEQ ID No. 3. This sequence had a homology of 20% and 16% with pGAT4 and pGAT106, respectively, at the level of amino acid sequence.

Example 9

Extraction of Crude Enzyme Solution from Perillas

Young red leaves were harvested from the plant bodies of Perilla ocimoides var. Akachirimen, and a crude enzyme solution was extracted according to the method as set forth in Example 1(2). This was reacted with 50 μl of a mixture containing, at a final concentration, 50 mM potassium phosphate, pH 8.5, 0.48 mM delphinidin 3,5-diglucoside, 0.43 mM caffeoyl-CoA and 20 μl of the enzyme solution at 30° C. for 10 minutes. 50 μl of acetonitrile containing 13.8% acetic acid was added to the reaction mixture to stop the reaction. After centrifuging at 15000 rpm for 5 minutes, a 10 μl aliquot of the supernatant was analyzed by HPLC under the following conditions.

The column used was the YMC-Pack ODS-A (6.0×15 cm), and samples were separated under the condition of 0.1% trifluoroacetic acid, 21.6% acetonitrile, and a flow rate of 1 ml/min. Detection was carried out at 520 nm. Under this condition unreacted delphinidin 3,5-diglucoside was eluted at 3 minutes and the one in which caffeic acid was transferred to position 3 of delphinidin 3,5-diglucoside was eluted at 4.7 minutes, the absorption maximum of said compound being 531 nm.

Modification by caffeic acid was also seen when delphinidin 3-glucoside was used as the substrate. Furthermore, when coumaroyl-CoA was used as a donor of acyl group, transfer of a coumaroyl group was observed. It was revealed that although natural perillas do not contain delphinidin glucoside as anthocyanin, the acyltransferase of perillas can use delphinidin 3-glucoside and delphinidin 3,5-diglucoside as the acyl group recipient and coumaroyl-CoA as the acyl group donor.

Example 10

Purification of the Acyltransferase Derived from Perillas

Purification of the acyltransferase derived from perillas was carried out in accordance with the method described in Example 2(1). Three kilograms of leaves of perillas was frozen in liquid nitrogen and pulverized frozen in a homogenizer. The pulverized material was homogenized again in 10 liters of the extraction buffer (100 mM sodium phosphate, pH 6.8, 10 mM sodium ascorbate, 5 mM dithiothreitol, 10 μM p-APMSF, 5% (w/v) polyclar SB-100) in a homogenizer. This was filtrated with gauze stacked in four layers, and then centrifuged (8,000 rpm, 4° C., 30 minutes). Ammonium sulfate was added to the supernatant to a 40% saturation. After dissolution, centrifugation is repeated under the same condition. Ammonium sulfate was added to the supernatant to a 70% saturation. After dissolution, centrifugation is repeated under the same condition. The precipitate was dissolved in a minimum amount of the desalting buffer (bis Tris-HCl, pH 6.3, 1 mM dithiothreitol, 10 μM p-APMSF, 10% glycerol), and then desalted by Sephadex G-25 medium (Pharmacia, 9.5×45 cm) which had been equilibrated with the same buffer.

The desalted sample was subjected to ion exchange chromatography using Q-Sepharose Fast Flow 26/10. A linear gradient of sodium chloride from 0 to 0.5 M in the desalting buffer was run at a flow rate of 8 ml/min over 1 hour. The active fractions were eluted at NaCl concentrations of about 0.15 to 0.3 M. The active fractions were adsorbed to four HiTrap Blue (5 ml) columns connected in a series which had been equilibrated with the desalting solution. After adequately washing the columns with the same buffer, elution was carried out by a linear gradient of sodium chloride from 0 to 1 M in the desalting buffer (2 hours, flow rate 5 ml/min). The active fractions were eluted at NaCl concentrations of 0.8 to 0.9 M. These fractions were subjected to chromatography using a hydroxyapatite column (ceramic type II 40 mm; Bio-Rad). The column on which a sample had been applied was adequately washed with buffer A (50 mM sodium phosphate, pH 6.8, 1 mM dithiothreitol, 10 μM p-APMSF, 10% glycerol). Then enzyme was eluted with a liner gradient from buffer A to buffer B (400 mM sodium phosphate, pH 6.8, 1 mM dithiothreitol, 10 μM p-APMSF, 10% glycerol), which eluted at about 0.2 M sodium phosphate. This active fractions were used for biochemical characterization of the enzyme.

In a similar manner to when the crude enzyme sample was used, any of cyanidin 3-glucoside, cyanidin 3,5-diglucoside, delphinidin 3-glucoside, and delphinidin 3,5-diglucoside could be used as the acyl group recipient. As the acyl group donor coumaroyl-CoA and caffeoyl-CoA could be used. The molecular weight was found to be about 50,000 by SDS-polyacrylamide gel electrophoresis. The isoelectric point was determined to be 5.3 using a Mono-P column (Pharmacia).

Example 11 cDNA Cloning of the Acyltransferase Derived from Perillas

By comparing the structures of pGAT4, pGAT106, and pGAT48 which were cloned in Example 3, Example 6, and Example 8, respectively, it was found that the amino acid sequence: Asp-Phe-Gly-Trp-Gly-Lys (SEQ ID No. 21) have been conserved. Accordingly, it is expected that this structure is also conserved in acyltransferases. Based on this sequence, nucleotide sequence: 5'-GA(TC)TT(TC)GGITGGGGIAA-3' (SEQ ID No. 22) was synthesized and this oligonucleotide was used as an ATC primer.

From young leaves of perillas, RNA was extracted in the method as described in Example 3 and a cDNA library was also constructed using the ZAP-cDNA synthesis kit (Stratagene). Using 50 ng of double stranded cDNA which was formed here as the template and 100 ng each of the ATC primer and the oligo 2 primer, PCR reaction was carried out in a final volume of 50 μl using the PCR kit (Takara Shuzo). The reaction was carried out for 25 cycles with one cycle comprising 95° C. for 1 minute, 50° C. for 1 minute, and 72° C. for 1 minute. A DNA fragment of about 400 bp thus obtained was recovered and cloned into a vector using the TA cloning kit (Invitrogen). Determination of the nucleotide sequence of the clone obtained revealed that the clone designated as pSAT104 had a high homology with pGAT4.

Using 10 ng of pSAT104 as the template and 100 ng each of the ATC primer and the oligo 2 primer, PCR reaction was carried out using the PCR kit (Takara Shuzo K.K.) in a final volume of 50 μl. The reaction was carried out for 15 cycles with one cycle comprising 95° C. for 1 minute, 50° C. for 1 minute, and 72° C. for 1 minute. Using 1 μl of this product and 100 ng each of the ATC primer and the oligo 2 primer, PCR reaction was carried out using the PCR kit in a final volume of 50 μl.

However, 4 μl of the DIG-labelled nucleotide solution (manufactured by Boehringer) was used here as the deoxynucleotide solution. After the reaction was complete, 5 μl of 3 M sodium acetate and 100 μl of ethanol were added to carry out ethanol precipitation. The product obtained was used for the subsequent study.

Using the labelled DNA fragment derived from pSAT104, the cDNA library of leaves of perillas was screened by the plaque hybridization technique. Washing was carried out in 1×SSC at 65° C. for 1 hour. Determination of the nucleotide sequence of the hybridized clone revealed that the clones of pSAT206, pSAT207, pSAT208, pSAT209, pSAT210, etc. contains the nucleotide sequence of pSAT104. When the nucleotide sequence of the 5' ends of these clones were compared with that of pGAT4, every clone had an amino terminal shorter than pGAT4 and none had the initiation codon. The nucleotide sequences of 5' ends of pSAT206 and pSAT208, and pSAT209 and pSAT210 were identical. pSAT207 was shorter than pSAT206 by 6 residues, and pSAT209 was shorter than pSAT206 by 5 residues.

On the vector pBluescript SK−, these cDNA's are taking such forms that enable them to fuse to the LacZ gene of the vector. Out of the above-mentioned clones, pSAT206, pSAT208, and pSAT207 are taking such shapes that enable them to express as a fusion protein with β-galactosidase, whereas pSAT209 and pSAT210 have shifted frames so that they cannot form a fusion protein.

pSAT206, pSAT207, pSAT209, and pSAT210 were expressed in *E. coli*, and then tested for the enzymatic activity of acyl group transfer to position 3 of glucose using delphinidin 3,5-diglucoside and caffeoyl-CoA. The method for inducing expression etc. was carried out in accordance with the method as set forth in Example 4.

The *E. coli* 's containing pSAT209 and pSAT210 did not exhibit any enzymatic activity of transferring acyl groups, but the *E. coli* containing pSAT206 exhibited the enzymatic activity of acylating 48% of delphinidin 3,5-diglucoside and the *E. coli* containing pSAT207 exhibited a similar enzymatic activity of acylating 24% of said compound. These results demonstrated that pSAT206, pSAT207, and the like reveal cloning of the gene having the enzymatic activity of transferring acyl groups to glucose at position 3 of anthocyanin of perillas.

Among these clones, the nucleotide sequence derived from cDNA of pSAT208 was determined. This is shown in the sequence listing SEQ ID No. 4. The amino acid sequence deduced from the nucleotide sequence exhibited a homology of 37%, 29%, and 15% with pGAT4, pGAT106, and pPAT48, respectively. As described hereinbefore, this sequence, though not a full-length cDNA, can express active enzymes by providing a suitable initiation codon as a fusion gene with LacZ.

By comparing the amino acid sequences of acyltransferases which were elucidated by the present invention, the conserved sequence was clarified. Based on the amino acid sequence of this region, it is possible to clone acyltransferases which modify sugars at other positions of anthocyanins.

Example 12 cDNA Cloning of the Acyltransferase Derived from Cinerarias

From petals of *Senecio cruentus* var. *Jupiter* Blue (Sakata Seed Corp.), RNA was extracted by the method as set forth in Example 3 above and Poly A+RNA was further purified. A cDNA library was constructed using the ZAP-cDNA synthesis kit (Stratagene).

Using 50 ng of double stranded cDNA which was formed here as the template and 100 ng each of the ATC primer and the oligo 2 primer, PCR reaction was carried out in a final volume of 50 µl using the PCR kit (Takara Shuzo). The reaction was carried out for 25 cycles with one cycle comprising 95° C. for 1 minute, 50° C. for 1 minute, and 72° C. for 1 minute. DNA fragments of about 400 bp thus obtained were collected and cloned into a vector using the TA cloning kit (Invitrogen). Determination of the nucleotide sequence of clones obtained revealed that a clone designated as pJAT4-had a high homology with pGAT4.

Then the cDNA library of petals of cinerarias was screened with pJAT4. Several clones were obtained. When the amino acid sequences deduced from the nucleotide sequences of the 5' end of these cDNA's were compared with the sequence of the protein encoding pGAT4, none of cDNA of the clones of cinerarias were full-length. Among them the entire nucleotide sequence of cDNA of the clone termed pCAT8 was determined. This is shown in the sequence listing SEQ ID No. 5. The amino acid sequence deduced from the nucleotide sequence obtained exhibited a homology of 28%, 35%, 16%, and 37% with pGAT4, pGAT106, pPAT48, and pSAT208, respectively.

Example 13

Construction of a Binary Vector Containing the Gene of the Acyltransferase Derived from *Gentian*

After the acyltransferase gene of gentians, pGAT4, was completely digested with KpnI, a DNA fragment of about 1.6 kb which is obtained by partial digestion thereof with XbaI was collected. This DNA fragment was subcloned using the restriction enzyme recognition sites, KpnI and XbaI, of pUC19 to obtain a plasmid pUCGAT4. After pUCGAT4 was completely digested with BglII, it was partially digested with SacI to collect a DNA fragment of about 0.95 kb. A plasmid obtained by ligating this DNA fragment, about 0.75 kb DNA fragment obtained by digestion of pUCGAT4 with XbaI and BglII, and a DNA fragment obtained by digestion of plasmid p2113G (described, for example, in Aida et al., Acta Horticulture, 392: 219–225, 1995) with XbaI and SacI was designated as pBEGA4. This plasmid is a binary vector, and the gentian acyl transferase cDNA is under the control of the cauliflower mosaic virus $^{35}$S promoter having enhancers and the nopaline synthase terminator within plant cells. It also has a translation enhancer called Ω sequence at the 5' end of cDNA of the gentian acyltransferase. It is noted that the promoter and terminator as used herein are not limited to those just described, but they may be a constitutive promoter or a promoter which specifically works in petals such as the promoter of the gene of chalcone synthase.

Example 14

Introduction of the Acyltransferase Gene Derived from *Gentian* into Plants pBEGA4 was introduced into *Agrobacterium tumefaciense* strain Ag10 (Lazo et al., Bio/Technology, 9: 963–967, 1991) by the method described in Plant Molecular Biology Manual (Kluwer Academic Publishers). On the other hand, by culturing a shoot apex of a rose var. *Lavende* in a solid medium in which BA (6-benzyl aminopurine) 2.25 mg/l, GA3 (gibberellic acid) 3.46 mg/l, sucrose 30 g/l, and Gellan Gum 2 g/l were added to the MS medium to obtain Embriogenic Callus (EC). An overnight culture of the above AG10 strain in the LB medium was suspended to the MS liquid medium containing 20 µg/ml of acetosyringone to adjust to a concentration of $5 \times 10^{\square}$ cells/ml. After immersing the EC in this bacterial culture liquid, excess liquid was wiped clean by sterilized filter paper. By transplanting and culturing in the MS medium in which BA 2.25 mg/l, GA3 0.35 mg/l, sucrose 30 g/l, and Gellan Gum 2 g/l were added to the MS medium, a transformant can be obtained. From the kanamycin resistant callus obtained, RNA was obtained using trizol (Lifetec Oriental). Using this RNA as the template, and nucleotide GAT-1: 5'-TGGCAACTGTCTTGCGT-CATG-3' (SEQ ID No. 23) and nucleotide GAT-2: 5'-CCAT-GTCAGGTGTGAGGTTCAAC-3' (SEQ ID No. 24) synthesized based on the nucleotide sequence of pGAT4 as the primer, RT-PCR reaction was carried out using the Access RT-PCR System (Promega). Using the same RNA as the template, and oligonucleotide Kan-1: 5'-ATCGTTTCGCAT-GATTGAAC-3' (SEQ ID No. 25) and oligonucleotide Kan-2: 5'-TCAGAAGAACTCGTCAAGAA-3' (SEQ ID No. 26) synthesized based on the nucleotide sequence of nptII on the binary vector as the primer, RT-PCR reaction was similarly carried out. The reaction was carried out for 40 cycles with one cycle comprising 94° C. for 30 seconds, 60° C. for 1 minute, and 68° C. for 2 minutes. From the callus of the transformant a band derived from pGAT4 and a band derived from nptII were observed, but from the callus of the non-transformant no bands corresponding to the above were observed. The result indicates that the gene of acyltransferase of gentians could be introduced into the rose.

Construction of the binary vector mentioned above and its transformation into a plant are not limited to the gene of acyltransferase of gentians contained in pGAT4, but other acyltransferases can be introduced into plants and genes thereof can be expressed in plants. As a species of a plant, a rose was described hereinabove. But since methods of transformation have been reported for many other plants (for example, carnations, chrysanthemums, tobaccos, petunias, gerberas, petunias, etc.), acyltransferase could be introduced into many plant species by employing published methods.

Example 15

Synthesis of the Full-Length cDNA of the Acyltransferase Derived from Perilla

The cDNA of acyltransferase gene of perillas, pSAT208, encodes active enzymes as described above, but it was not full-length. Accordingly, a full-length cDNA containing the initiation codon was synthesized based on the nucleotide sequence of acyltransferase gene of gentians, pGAT4. Thus, the DNA shown below was synthesized. The amino acid sequence encoded by the DNA is also shown. The first underline means a BamHI recognition sequence, and the next underline means a sequence contained in pSAT208. Behind the BamHI recognition sequence is inserted a sequence AACA which often occurs immediately before the translation initiation codon in plants.

5' G<u>GGATCC</u>AACA ATG GAG CAA ATC CAA ATG GTG <u>GCCGTGATCGAAACGTGTAGA</u> 3'Met Glu Gln Ile Gln Met Val Ala Val Ile Glu Thr Cys Arg (SEQ ID No. 27 and 38 respectively)

PCR reaction was carried out in a final volume of 50 µl containing 100 ng each of this primer and −20 primer: 5'-GTAAAACGACGGCCAT-3' (SEQ ID No. 28), and 10 ng of pSAT208. The reaction was carried out for 15 cycles with one cycle comprising 95° C. for 1 minute, 55° C. for 1 minute, and 72° C. for 2 minutes. After the reaction, DNA fragments were recovered from the reaction mixture using GENECLEAN (Biol01) by the method recommended by the manufacturer. After digesting the recovered DNA with BamHI and EcoRI, followed by agarose gel electrophoresis, a DNA fragment of about 200 bp was recovered. This DNA fragment was ligated to a DNA fragment of about 3.3 kb obtained by digesting pSAT208 with EcoRI and the plasmid obtained was termed pSATF208. The nucleotide sequence of this plasmid was determined from 5' end of the cDNA to confirm the nucleotide sequence.

Example 16

Expression of the Gene of the Acyltransferase Derived from Perillas in Yeast

In accordance with the method described in Example 5, pSATF208 was expressed in yeast and tested for enzymatic activity. Thus, a plasmid obtained by ligating a DNA fragment of about 8 kb obtained by digestion of pYE22m with BamHI and SalI with a DNA fragment of about 8 kb obtained by digestion of pSATF208 with BamHI and SalI was termed pYSAT208.

Yeast G1315 was transformed with pYSAT208 and the activity of acyltransferase of the resulting transformant was determined. As a result, in the yeast into which pYSAT208 was introduced, formation of 10 nmole of delphinidin 3-caffeoylglucoside 5-glucoside from 24 nmol of delphinidin 3,5-diglucoside and 21.5 nmol of caffeoyl-CoA was observed. Thus, it was confirmed that the synthesized full-length cDNA cotained in pSATF208 encodes the activity of acyltransferase.

Example 17

Construction of a Binary Vector Containing the Acyltransferase Gene Derived from Perillas Plasmid pE12ΩGUS is one in which the expression unit of GUS gene on plasmid p2113G (Aida et al., Acta Horticulture, 392: 219–225, 1995) has been inserted into the HindIII and EcoRI recognition sites of pUC19. After pE12ΩGUS was digested with SacI and blunt-ended using the DNA blunting kit (Takara Shuzo), it was ligated to an XhoI linker (Toyobo). The plasmid obtained which has an XhoI linker inserted thereinto was termed pE12ΩGUSx. A plasmid obtained by ligating about 2.8 kb DNA fragment obtained by digestion of this plasmid with HindIII and EcoRI to pBin19 digested with HindIII and EcoRI was designated pBEGUSx. A plasmid obtained by ligating a DNA fragment of about 11 kb obtained by digestion of BEGUSx with BamHI and XhoI to a DNA fragment obtained by digestion of pSATF208 with BamHI and XhoI was termed pBESA208. On this plasmid the acyltransferase of perillas is under the control of the cauliflower mosaic virus 35S promoter having enhancers and the nopaline synthase terminator.

Example 18

Introduction of the Acyltransferase Gene of Perillas into Plants pBESA208 was introduced into *Agrobacterium tumefacience* strain Ag10 (Lazo et al., Bio/Technology, 9: 963–967, 1991) by the method described in Plant Molecular Biology Manual (Kluwer Academic Publishers). Ag10 strain transformant was used to transform petunia Falcon red (Sakata Seed Co.), Baccarat red (Sakata Seed Co.), and Titan red (Sakata Seed Co.) by the method described in Plant Molecular Biology Manual (Kluwer Academic Publishers). These Petals of petunia contain cyanidin-3-glucoside as a major anthocyanin.

Transformation was also carried out to a rose var. *Lavande* by the above-mentioned method.

Example 19

Synthesis of the Full-Length cDNA of the Acyltransferase Derived from Cinerarias The cDNA of cineraria acyltransferase gene, pCAT208, as hereinabove described, was not full-length. Accordingly, a full-length cDNA containing the initiation codon was synthesized based on the nucleotide sequence of the gentian acyltransferase gene, pGAT4. Thus, the DNA shown below was synthesized. The amino acid sequence encoded by the DNA is also shown. The first underline means a BamHI recognition sequence for cloning, and the next underline means a sequence contained in pCAT208.

5' G<u>GGGATCC</u>AACA ATG GAG CAA ATC CAA ATG G<u>TGAACATTCTCGAAC</u> 3'Met Glu Gln Ile Gln Met Val Asn Ile Leu Glu (SEQ ID No. 29 and 39 respectively)

PCR reaction was carried out in a final volume of 50 µl containing 100 ng each of this primer and −20 primer, and 10 ng of pCAT8. The reaction was carried out for 15 cycles with one cycle comprising 95° C. for 1 minute, 55° C. for 1 minute, and 72° C. for 2 minutes. After the reaction was over, DNA fragments were recovered from the reaction mixture using GENECLEAN (Biol01) by the method recommended by the manufacturer. After digesting the recovered DNA with BamHI and MvaI, followed by agarose gel electrophoresis, a DNA fragment of about 200 bp was recovered. This DNA fragment was ligated to a DNA fragment of about 1.3 kb obtained by digesting pCAT8 with MvaI and XhoI and plasmid pBluescript SK− digested with BamHI and XhoI, and the plasmid obtained was termed pCATF208. The nucleotide sequence of this plasmid was determined from the 5' end of the cDNA to confirm the nucleotide sequence.

Example 20

Cloning of cDNA Encoding the Acyltransferase Derived from Lavenders

A cDNA library derived from petals of lavender of the *perilla* family, *Lavandula angustifolia*, was constructed by the method as set forth in Example 3, and screened by the plaque hybridization technique detailed in Example 3. About 300,000 clones were screened. Thus, the probe used was obtained by carrying out PCR reaction in a final volume of 50 µl using 100 ng each of the synthetic nucleotide RI primer:

5'-CTCGGAGGAATTCGGCACGAC-3' (SEQ ID No. 30) and the oligo 2, 10 ng of pSAT208, and a DIG-labelled nucleotide as the nucleotide. The reaction was carried out for 25 cycles with one cycle comprising 95° C. for 1 minute, 50° C. for 1 minute, and 72° C. for 2 minutes.

The labelled cDNA fragment was added to the hybridization solution and hybridization was carried out at 37° C. for further 16 hours. The filter was washed with the washing solution (5×SSC, 1% SDS) and then an enzymeimmunoassay (Boehriner Mannheim) using the DIG-specific antibody labelled with alkaline phosphatase was carried out to detect positive clones by color development using 5-bromo-4-chloro-3-indolyl phosphate and nitroblue tetrazolium salt. The detection method used was as set forth in the manufacturer's instructions.

As a result, one positive clone was obtained. This cDNA was rescued in the form which employs plasmid pBluescript SK− as a vector from the form which employs λ phage as the vector using the method recommended by the manufacturer. A plasmid was extracted from the clone obtained and was termed pLART1. As described above, the nucleotide sequence in the vicinity of the 5' end of cDNA of pLAT1 was determined using the ABI373 DNA Sequencer (Perkin Elmer) by the pigment deoxy sequence method with the fluorogenic pigment recommended by the manufacturer. The amino acid sequence deduced from the nucleotide sequence thus obtained has a high homology with the amino acid sequence of acyltransferase of perillas and gentians, suggesting that pLAT1 encodes the acyltransferase of lavenders. But, the amino acid sequence encoded by pLAT1 is shorter than that of acyltransferase of perillas or gentians and it is, conceivably, not long enough to encode the entire length of acyltransferase. Accordingly, using the cDNA fragment of pLAT1 labelled with DIG as the probe, the cDNA library of lavenders was screened under the same condition mentioned above. The probe was labelled by the PCR reaction in a final volume of 50 µl containing about 1 ng of pLAT1 plasmid as the template, 500 ng each of the RI primer described below and the oligo 2, and 8 µl of dNTP-labelled mixture (Boehringer). The PCR reaction was carried out for 25 cycles with one cycle comprising 95° C. for 1 minute, 42° C. for 2 minutes, and 72° C. for 3 minutes, and the reaction was kept at 72° C. for 7 more minutes in order to perfect the elongation reaction. The plaque hybridization was carried out by the method described above except that the concentration of formamide in the hybridization buffer was 50% and that the filter was washed with 2×SSC and 1% SDS. The nucleotide sequence in the vicinity of the 5' end of cDNA of the positive clone obtained was determined as described above, and a clone, pLAT21, which is 11 bp longer than pLAT1 was obtained. This is shown in the sequence listing SEQ ID No. 6. However, pLAT21 did not contain the methionine initiation codon either and was not long enough to encode the entire length.

Example 21

Synthesis of the Full-Length cDNA of the Acyltransferase Derived from Lavenders

Since the cDNA, pLAT21, which is considered to encode the acyltransferase of lavenders does not contain the methionine initiation codon, the methionine initiation codon must be added to the 5' end of the cDNA in order to permit its expression in yeast. Accordingly, using a primer as described below, PCR reaction was carried out to synthesize a fragment in which the methionine initiation codon has been added to the 5' end of pLAT21. The primer LAT-ATG is designed so that it contains, in addition to 20 nucleotide sequences at the 5' end of pLAT21, the methionine initiation codon, the conserved sequence AACA for gene expression in plant which is believed to be present adjacent to the upstream thereof and the restriction enzyme BamHI recognition site required for ligation to a yeast expression vector in the direction of 5' upstream to 3'. The LAT-ATG primer (SEQ ID No. 31) and peptide encoded thereby (SEQ ID No. 40):

5'-AGTC<u>GGATCC</u>AACA A<u>TGACCACCCTCCTCGAATCC</u> 3'Thr Thr Leu Leu Glu Ser

PCR reaction was carried out in a final volume of 50 µl containing about 100 ng of the pLAT21 plasmid as the template, and 500 ng each of the LAT-ATG primer and the oligo 2 primer. PCR reaction was carried out for 10 cycles with one cycle comprising 95° C. for 1 minute, 42° C. for 2 minutes, and 72° C. for 3 minutes, and the reaction was kept at 72° C. for 7 more minutes in order to perfect the elongation reaction. The DNA fragment thus obtained was cleaved with BamHI and EcoRI and a DNA fragment of about 550 bp was recovered. This DNA fragment was subcloned into the BamHI and EcoRI sites of the plasmid vector plasmid pBluescript SK− and termed pLATPCR11. The nucleotide sequence of pLATPCR11 was determined as mentioned before, and it was confirmed that this PCR-amplified DNA fragment had the same sequence as that of from the 5' end to EcoRI site of pLAT21 cDNA, and contained the methionine initiation codon in the LAT-ATG primer and the conserved sequence for gene expression in plants, and the restriction enzyme BamHI recognition site required for ligation to a yeast expression vector.

Furthermore, the entire nucleotide sequence of pLAT21 was determined in a similar method to the one used to determine the nucleotide sequence of cDNA of pGAT4. The amino acid sequence expected to be encoded by this cDNA had a homology of 69%, 38%, 37%, 37%, and 19% with pSAT208, pGAT4, pGAT8, pGAT106, and pPAT48, respectively.

Example 22

Expression of the Acyltransferase Gene Derived from Lavenders in Yeast

A plasmid obtained by ligating a DNA fragment of about 550 bp cleaved out from pLATPCR11 with BamHI and EcoRI, a DNA fragment of about 1 kb obtained by cleavage of pLAT21 with EcoRI and XhoI, and a DNA fragment of about 8 kb obtained by cleavage of pYE22m with BamHI and SalI was designated as pYELAT21. As hereinabove explained, yeast G1315 was transformed with this plasmid and the activity of acyltransferase was determined.

As a result, in the yeast into which pYELAT21 was introduced, formation of 19.9 nmol of delphinidin 3-caffeoylglucoside 5-glucoside from 24 nmol of delphinidin 3,5-diglucoside and 21.5 nmol of caffeoyl-CoA was observed. Thus, it was confirmed that the synthesized full-length cDNA cotained in pYELAT21 encodes the activity of acyltransferase.

Example 23

Construction of a Binary Vector Containing the Acyltransferase Gene Derived from Lavenders A plasmid obtained by ligating a DNA fragment of about 550 bp cleaved out from pLATPCR11 with BamHI and EcoRI, a DNA fragment of about 1 kb obtained by cleavage of pLAT21 with EcoRI and XhoI, and a DNA fragment of about 11 kb obtained by digestion of pBEGUSx with BamHI and XhoI was designated as pBELA11. As hereinabove explained, this was transformed into *Agrobacterium tumefacience* strain Ag1 0 and was supplied for transformation of petunias and roses.

Example 24

Construction of Antibody Against Acyltransferase

As a means to obtain the gene of an enzyme whose amino acid sequence is similar to that of the desired enzyme, there is mentioned a method in which the cDNA library of the expression form is screened by antibody to an enzyme. In this case, an antibody against the acyltransferase encoded by pGAT4 of gentians was produced. Similarly, it is possible to produce antibodies to other acyltransferases.

First, using the Bulk and RediPack GST Purification Modules (pharmacia Biotech), the GAT4 protein was expressed in large quantities using *E. coli*, from which the antibody was purified.

(1) Construction of Expression Plasmid pGEX-4T-1 was used to express the acyltransferase gene in *E. coli*. Using this pGEX-4T-1 a fusion protein with glutathione S-transferase can be prepared, which is purified efficiently using an affinity column of glutathione S-transferase.

After pGEX-4T-1 was digested with SmaI and XhoI, it was blunt-ended using the DNA blunting kit (Takara Shuzo). The DNA fragment of about 4.9 kb thus obtained was dephosphorylated using alkaline phosphatase BAP C75 (Takara Shuzo). A DNA fragment of about 1.6 kb obtained by digestion of pGAT4 with SmaI and KpnI present in said vector was blunt-ended as described before, and was recombined with the above-mentioned the blunt-ended site after digestion of pGEX-4T-1 with SmaI and XhoI to construct pGEXGAT4. By digesting with EcoRI and BglII, it was confirmed that the cDNA and glutathione S-transferase on pGAT4 were in the same direction.

(2) Expression of Acyltransferase in *E. coli*

E. coli strain JM109 was transformed with pGEXGAT4. Tansformation of *E. coli* was carried out by the method of Hanahan (J. Mol. Biol, 166: 557-, 1983). The transformed *E. coli* was inoculated to 50 ml of 2×YT medium (tryptone 16 g, yeast extract 10 g, and sodium chloride 5 g were dissolved into one liter of distilled water, and then pH was adjusted to 7.0 with sodium hydroxide) containing ampicillin (100 µg/l) and 2% glucose, and then cultured overnight at 37° C. Forty ml of the culture was inoculated into 40 ml of 2×YT medium containing ampicillin (100 µg/l) and 2% glucose, followed by incubation at 37° C. for 3 hours, to which 440 µl of IPTG (final concentration 10 mM) was added and cultured for 5 more hours. After harvesting, the cells were suspended to 100 ml of 1×PBS (sodium chloride 8.2 g, potassium chloride 2.0 g, disodium hydrogen phosphate 1.43 g, and potassium dihydrogen phosphate 2.45 g were dissolved in one liter of distilled water) containing 10 µM of APMSF. After the suspension was disrupted by sonication, 5 ml of 20% Triton X-100 was added (final concentration 1%). After shaking in ice for 30 minutes, it was centrifuged at 12,000 rpm for 10 minutes. The precipitate obtained was suspended to 12 ml of 6 M urea, to which was added an equal amount of 2×SDS sample buffer and treated at 90° C. for 5 minutes to prepare a sample.

This sample (0.8 ml) was separated on disk gel electrophoresis (separating gel 7.5% acrylamide, stacking gel 5% acrylamide: ATTO BIO PHORESISI III) and collected in aliquots of 0.8 ml. Each fraction was analyzed on SDS-polyacrylamide gel electrophoresis (separating gel 10% acrylamide, stacking gel 4.5% acrylamide). The result indicated that there was a fraction in which a protein having a molecular weight of about 75,000 corresponding to the size of a fusion protein of the acyltransferase and glutathione S-transferase encoded by pGAT4 was present as a single protein.

This fraction (3.2 ml) was concentrated by Centricon 10 (Amicon) to obtain about 0.3 µg of the fusion protein. Using this sample, antibody was produced using BALB/C mice by the conventional method. Using this antibody, a homologs of acyltransferase can be obtained.

INDUSTRIAL APPLICABILITY

As hereinabove described, in accordance with the present invention, aromatic acyltransferase derived from gentians was purified, the cDNA of said enzyme was cloned, and the nucleotide sequence of said cDNA was determined. Furthermore, by expressing the activity in *E. coli* and yeast, the separated cDNA was confirmed to be identical with the one encoding aromatic acyltransferase.

Thus, by connecting the cDNA according to the present invention to a suitable plant expression vector and then introducing it into a plant, it became possible to utilize acylation reaction in order to control the color of flowers.

Furthermore, by utilizing the present enzymatic activity, it is possible to modify the structures of anthocyanins in plants or in vitro in order to provide more stable anthocyanins.

The invention claimed is:

1. An isolated polynucleotide encoding an anthocyanin acyltransferase comprising an amino acid sequence selected from the group consisting of SEQ ID NO: 32, SEQ ID NO: 33, SEQ ID NO: 34, SEQ ID NO: 35, SEQ ID NO: 36, and SEQ ID NO: 37.

2. A vector comprising the polynucleotide according to claim 1.

3. A host cell transformed with the vector according to claim 2.

4. The host cell according to claim 3, wherein said host cell is a microbial cell or a plant cell.

5. The host cell according to claim 3, wherein said host cell is a plant cell.

6. A method for acylating a pigment in a plant, comprising introducing the polynucleotide according to claim 1 into a plant, whereby said polynucleotide expresses a protein, and said protein acylates the pigment in the plant.

7. A method for stabilizing a pigment in a plant, comprising introducing the polynucleotide according to claim 1 into a plant, whereby said polynucleotide expresses a protein, and said protein acylates the pigment in the plant, which stabilizes the pigment of said plant.

8. A method for altering color of flowers, comprising introducing the polynucleotide according to claim 1 into a plant, whereby said polynucleotide expresses a protein, and said protein acylates the pigment in the plant, which alters the color of flowers of said plant.

9. A plant, its progeny, or tissue of said plant or said progeny, each transformed with the polynucleotide according to claim 1.

10. A cut flower of a plant, or its progeny transformed with the polynucleotide according to claim 1, wherein the color of said flower is altered.

11. The method according to claim 7, wherein the pigment is anthocyanin.

12. The method according to claim 8, wherein the pigment is anthocyanin.

* * * * *